US012610893B2

(12) United States Patent
Boyer et al.

(10) Patent No.: US 12,610,893 B2
(45) Date of Patent: Apr. 28, 2026

(54) SYSTEMS AND METHODS FOR LONG-TERM POLLEN STORAGE

(71) Applicant: Monsanto Technology LLC, St. Louis, MO (US)

(72) Inventors: Zachary Boyer, Fenton, MO (US); Benjamin T. Julius, Saint Charles, MO (US); Yuechen Zhu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/679,358

(22) Filed: Feb. 24, 2022

(65) Prior Publication Data

US 2022/0287244 A1 Sep. 15, 2022

Related U.S. Application Data

(60) Provisional application No. 63/158,328, filed on Mar. 8, 2021.

(51) Int. Cl.
*A01G 7/00* (2006.01)
*A01H 1/02* (2006.01)

(52) U.S. Cl.
CPC ...... *A01G 7/00* (2013.01); *A01H 1/02* (2013.01)

(58) Field of Classification Search
CPC ... A01N 3/00; A01G 7/06; A01G 7/00; A01H 1/027; A01H 1/02; A23B 4/16; A23B 4/031; A23B 9/00; F26B 5/00
See application file for complete search history.

(56) References Cited

U.S. PATENT DOCUMENTS

| | | | |
|---|---|---|---|
| 10,575,517 | B2 | 3/2020 | Cope et al. |
| 2006/0179680 | A1 | 8/2006 | Miller et al. |
| 2008/0052954 | A1 | 3/2008 | Beaulac |
| 2015/0285775 | A1 | 10/2015 | Gurumohan et al. |

(Continued)

FOREIGN PATENT DOCUMENTS

CN 204086917 1/2015

OTHER PUBLICATIONS

Barnabas et al. Effect of pollen storage by drying and deep-freezing on the expression of different agronomic traits in maize (*Zea mays* L.); Euphytica 39, 1988; pp. 221-225.*

(Continued)

*Primary Examiner* — Kent L Bell

(74) *Attorney, Agent, or Firm* — Dentons US LLP; David Lanzotti

(57) ABSTRACT

The invention provides novel systems and methods for drying and storing pollen. The invention further provides novel methods for delivering pollen to a recipient plant. The systems provided herein include a chamber configured to permit a drying gas to contact pollen, a source for the drying gas, and an instrument configured to measure the humidity of the drying gas or a sensor configured to measure the moisture content of the pollen. The methods provided herein include methods of drying pollen to a desired moisture content, methods of storing dried pollen, and methods of applying the dried or stored pollen to at least a recipient plant, thereby pollinating the recipient plant with the dried or stored pollen from the donor plant.

22 Claims, 17 Drawing Sheets

(56)           References Cited

U.S. PATENT DOCUMENTS

| | | | |
|---|---|---|---|
| 2017/0238535 A1* | 8/2017 | Cope | A01N 3/00 |
| 2019/0008144 A1 | 1/2019 | Etter et al. | |

OTHER PUBLICATIONS

Barnabas et al.; Fertility of Deep-frozen Maize (*Zea mays* L.) Pollen; Annals of Botany; vol. 48, Issue 6; Dec. 1981; pp. 861-864.*

Barajas et al.; Effect of Temperature On The Drying Process of Bee Pollen From Two Zones of Colombia; Journal of Food Process Engineering; vol. 35; 2012; pp. 134-148.*

Barnabas, et al. Storage of maize (*Zea mays* L.) pollen at −196° C. in liquid nitrogen. Euphytica 25, 747-752 (1976).

Barnabas. Effect of Water Loss on Germination Ability of Maize (*Zea mays* L.) Pollen, Annals of Botany, vol. 55, Issue 2, Feb. 1985, pp. 201-204.

Barnabas, et al. Effect of pollen storage by drying and deep-freezing on the expression of different agronomic traits in maize (*Zea mays* L.). Euphytica 39, 221-225 (1988).

Barnabas. Preservation of Maize Pollen. In: Bajaj, Y.P.S. (eds) Maize. Biotechnology in Agriculture and Forestry, vol. 25. Springer, Berlin, Heidelberg. (1994).

Buitink, et al. Calorimetric Properties of Dehydrating Pollen (Analysis of a Desiccation-Tolerant and an Intolerant Species), Plant Physiology, vol. 111, Issue 1, May 1996, pp. 235-242.

Gorla, et al. Genetic variability of gametophyte growth rate in maize. Theoret. Appl. Genetics 46, 289-294 (1975).

Greenspan, et al. Humidity Fixed Points of Binary Saturated Aqueous Solutions. J Res NBS Phys Chem, 81A:89-96, 1977.

International Search Report and Written Opinion regarding International App. No. PCT/US2022/017600, dated Jun. 8, 2022.

Nath, et al. Effect of freezing and freeze-drying on the viability and storage of *Lilium longiflorum* L. and *Zea mays* L. pollen. Cryobiology (1975): vol. 12, Issue 1, pp. 81-88.

Pacini, et al. Pollen Developmental Arrest: Maintaining Pollen Fertility in a World With a Changing Climate. Front. Plant Sci., 10:679, May 24, 2019.

Pfahler, et al. In vitro germination and pollen tube growth of maize (*Zea mays* L.) pollen : VI. Combined effects of storage and the alleles at the waxy (wx), sugary (su 1)and shrunken (sh 2)loci. Theoretical Applied Genetics, 42(3), 136-140. (1972).

Rauf, et al. Breeding Strategies to Enhance Drought Tolerance in Crops. In: Al-Khayri, J., Jain, S., Johnson, D. (eds) Advances in Plant Breeding Strategies: Agronomic, Abiotic and Biotic Stress Traits. Springer, Cham. (2016).

Sartoris. Longevity of Sugarcane and Corn Pollen—A Method for Long-Distance Shipment of Sugarcane Pollen by Airplane. American Journal of Botany, 29(5), 395-400, (May 1942).

Borel et al., Performance evaluation of an infrared heating-assisted fluidized bed dryer for processing bee-pollen grains, Chemical Engineering and Processing: Process Intensification 155:108044, 2020.

Supplemental Partial European Search Report regarding EP App. No. 22767657, dated Jan. 13, 2025.

* cited by examiner 105
104
101
107
102
103
106

Drying Gas

Drying Gas

SYSTEMS AND METHODS FOR LONG-TERM POLLEN STORAGE

CROSS-REFERENCE TO RELATED APPLICATIONS

This application claims the priority of U.S. Provisional Appl. Ser. No. 63/158,328, filed Mar. 8, 2021, the entire disclosure of which is incorporated herein by reference.

FIELD OF THE INVENTION

The present disclosure relates to the field of agricultural biotechnology, and more specifically to systems and methods for long-term pollen storage.

BACKGROUND OF THE INVENTION

Pollen viability is influenced by environmental conditions and may decrease rapidly once shed. Methods to maintain or improve pollen viability and fertility following pollen storage would have significant value to the agricultural industry. Corn (*Zea mays*; also known as maize), rice (*Oryza sativa*), wheat (*Triticum aestivum*), and sorghum (*Sorghum bicolor*), which belong to the Poaceae family of plants, are examples of economically important agricultural crops in which breeding has been hampered by low efficiency procedures for long-term pollen storage. Pollen of plants from the Poaceae family is classified as recalcitrant or desiccation sensitive. Other non-limiting examples of recalcitrant pollen include pollen from certain species in the Alismataceae, Amaranthaceae, Cactaceae, Chenopodiaceae, Cucurbitaceae, Anacardiaceae, Portulacaceae, Urticaceae, Lauraceae, Liliaceae, Iridaceae, Orchidaceae, Acanthaceae, and Caryophyllaceae families. The long-term storage of pollen from such crops would provide significant advancements over the current state of the art in the fields of breeding and hybrid seed production. Successful long-term storage would allow breeders to conduct crosses between parents grown at different times and in different regions, which would significantly improve workflow and expand progeny diversity.

SUMMARY

In one aspect, the present disclosure provides a system for drying pollen comprising: a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and an instrument in fluid communication with the outlet configured to measure the humidity of the drying gas that enters the outlet. In one embodiment, the instrument is configured to obtain a plurality of humidity measurements. In another embodiment, the instrument is in electronic communication with a display unit capable of displaying the humidity measurement. In yet another embodiment, the instrument is in electronic communication with a processor configured to determine when the pollen has reached a desired moisture content. In still yet another embodiment, the processor is in electronic communication with an automated switch configured to stop the flow of the drying gas when the desired moisture content has been reached. In one embodiment, the system comprises a second instrument in fluid communication with the inlet configured to obtain at least one humidity measurement of the drying gas. In another embodiment, the second instrument is configured to obtain a plurality of humidity measurements. In yet another embodiment, the system further comprises a first thermometer in fluid communication with the outlet configured to measure the temperature of the drying gas that enters the outlet. In still yet another embodiment, the system further comprises a first thermometer in fluid communication with the outlet configured to measure the temperature of the drying gas that enters the outlet or a second thermometer in fluid communication with the inlet configured to measure the temperature of the drying gas that enters the inlet. In one embodiment, the system comprises the first thermometer and the second thermometer. Non-limiting examples of instruments that may be utilized as the first instrument or the second instrument include a chilled-mirror dewpoint sensor, a psychrometer, and a capacitance-based humidity sensor.

In another aspect, the present disclosure provides a system for drying pollen comprising: a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and a sensor configured to obtain at least one moisture content measurement of the pollen within the chamber. In one embodiment, the sensor is configured to obtain a plurality of moisture content measurements. In another embodiment, the sensor is in electronic communication with a display unit capable of displaying the moisture content measurement. In yet another embodiment, the sensor is in electronic communication with a processor configured to determine when the pollen has reached a desired moisture content. In still yet another embodiment, the processor is in electronic communication with an automated switch configured to stop the flow of the drying gas when the desired moisture content has been reached. In one embodiment, the at least one moisture content measurement is a wet basis moisture content measurement. In another embodiment, the at least one moisture content measurement is a dry basis moisture content measurement. Non-limiting examples of sensors that may be utilized in the present invention include a near infrared sensor, a nuclear magnetic resonance sensor, a microwave sensor, or a capacitance sensor.

In one embodiment, the drying gas is selected from the group consisting of air, nitrogen, oxygen, and argon. In another embodiment, the inlet comprises a first filter or the outlet comprises a second filter, wherein the first or second filter is permeable to the drying gas and impermeable to the pollen. In yet another embodiment, the inlet comprises the first filter and the outlet comprises the second filter. In still yet another embodiment, the first filter or the second filter has a pore diameter of less than about 150 μm. In one embodiment, the first filter or the second filter has a pore diameter of less than about 60 μm. In another embodiment, the pollen is further defined as a) pollen from a monocot plant; or b) recalcitrant pollen. In yet another embodiment, the pollen is from a cereal plant, non-limiting examples of which are a corn, rice, wheat, and sorghum plant.

In one embodiment, the desired moisture content is a wet basis moisture content between about 10% and about 35%. The desired wet basis moisture content may be for example about 10%, 15%, 20%, 25%, 30%, or 35%, including all ranges derivable therebetween. In another embodiment, the desired moisture content is a dry basis moisture content between about 17% and about 55%. In yet another embodiment, the desired dry basis moisture content is between about 17.6% and about 53.8%. The desired dry basis moisture content may be for example about 17%, 20%, 25%, 30%, 35%, 40%, 45%, 50%, or 55%, including all ranges derivable therebetween.

In still yet another embodiment, the system further comprises a controller configured to regulate the flow of the drying gas into the chamber. Non-limiting examples of controllers include a differential pressure mass flow controller, a thermal mass flow controller, and a Coriolis mass flow controller. In one embodiment, the system further comprises mass flow meter configured to measure the flow of the drying gas into the chamber.

In another aspect, a method for drying pollen is provided herein, the method comprising drying the pollen using the systems described herein. In one embodiment, the system comprises a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and an instrument in fluid communication with the outlet configured to measure the humidity of the drying gas that enters the outlet. In another embodiment, the system comprises a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and a sensor configured to obtain at least one moisture content measurement of the pollen within the chamber. In yet another embodiment, the method comprising obtaining at least one measurement that provides information regarding the moisture content of the pollen. In still yet another embodiment, the at least one measurement is a humidity measurement of the drying gas. In one embodiment, the at least one measurement is a wet basis moisture content measurement or a dry moisture content measurement of the pollen. In another embodiment, the at least one measurement is obtained prior to the drying. In yet another embodiment, the method comprises regulating the flow of the drying gas into the chamber. In still yet another embodiment, the method comprises determining the moisture content of the pollen prior to the drying. In one embodiment, the method comprises calculating the mass flow rate of water exiting the chamber. In another embodiment, the method comprises determining when the pollen has reached a desired moisture content. In yet another embodiment, the determining comprises calculating the slope of the change in the moisture content of drying gas from the outlet. In one embodiment, the determining is performed by a processor in electronic communication with the instrument or the sensor. In another embodiment, the method comprises stopping the flow of the drying gas into the chamber when the desired moisture content has been reached. In yet another embodiment, the stopping is automated. In still yet another embodiment, the desired moisture content is a wet basis moisture content between about 10% and about 35%. In one embodiment, the desired moisture content is a dry basis moisture content between about 17% and about 55%. In yet another embodiment, the method comprises transmitting an electronic signal in response to obtaining at least one measurement. In still yet another embodiment, the method comprises collecting pollen from the chamber following the drying.

In yet another aspect, a method of storing pollen is provided here, the method comprising: (a) obtaining pollen according to the methods of drying the pollen using the systems described herein; and (b) storing the pollen. In one embodiment, the system comprises a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and an instrument in fluid communication with the outlet configured to measure the humidity of the drying gas that enters the outlet. In another embodiment, the system comprises a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and a sensor configured to obtain at least one moisture content measurement of the pollen within the chamber. In yet another embodiment, the storing is performed at a temperature between about −196° C. and about −60° C. or at a temperature between about −196° C. and about −70° C. The storage temperature may be, for example, about −196° C., −190° C., −180° C., −170° C., −160° C., −150° C., −140° C., −130° C., −120° C., −110° C., −100° C., −90° C., −80° C., −76° C., −75° C., −70° C., −65° C., or −60° C., including all ranges derivable therebetween. In a particular embodiment, the storage temperature is less than about −60° C. In still yet another embodiment, the storing is performed for up to about 1 year, 5 years, 10 years, 15 years, 20 years, 25 years, or 30 years or more, including all ranges derivable therebetween. In other embodiments, the storing may be performed for at least about 15 minutes, 1 hour, 12 hours, 1 day, 1 week, 1 month, 6 months, 1 year, 2 years, 5 years, 7 years, or 10 years or more, including all ranges derivable therebetween. In one embodiment, at least about 1%, 2%, 3%, 4%, or 5% of pollen grains remain capable of germination on a stigma following the storing, including all ranges derivable therebetween. In another embodiment, the pollen is defined as a) pollen from a monocot plant; or b) recalcitrant pollen. In yet another embodiment, the pollen is from a cereal plant, non-limiting examples of which include a corn, rice, wheat, and sorghum plant.

In still yet another aspect, a method for pollinating a plant is provided herein, the method comprising: (a) obtaining pollen according the methods of drying or storing pollen provided herein; and (b) pollinating the plant with the pollen. In one embodiment, the pollinating produces at least about 1 seed. In another embodiment, the pollinating produces at least about 1 seed per some amount of pollen, including one pollen grain, or 0.5 mg, 1 mg, 2 mg, 3 mg, 4 mg, or 5 mg of pollen used for the pollinating. In yet another embodiment, the pollinating produces a substantially equivalent number of seeds compared to the number of seeds produced from pollination under the same conditions but using pollen that was not subject to drying storing.

In one aspect, a system for drying pollen is provided herein comprising a sensor configured to obtain at least one moisture content measurement of the pollen during the drying, wherein the sensor is in electronic communication with a processor configured to determine when the pollen has reached a desired moisture content.

In another aspect, a method for drying pollen is provided herein comprising: a) drying pollen; b) obtaining at least one measurement that provides information regarding the moisture content of the pollen; and c) determining when the pollen has reached a desired moisture content. In one embodiment, the drying of the pollen is stopped when the pollen has reached the desired moisture content.

BRIEF DESCRIPTION OF DRAWINGS

Those of skill in the art will understand that the drawings, described below, are for illustrative purposes only. The drawings are not intended to limit the scope of the present teachings in any way.

DETAILED DESCRIPTION

Figure 1:
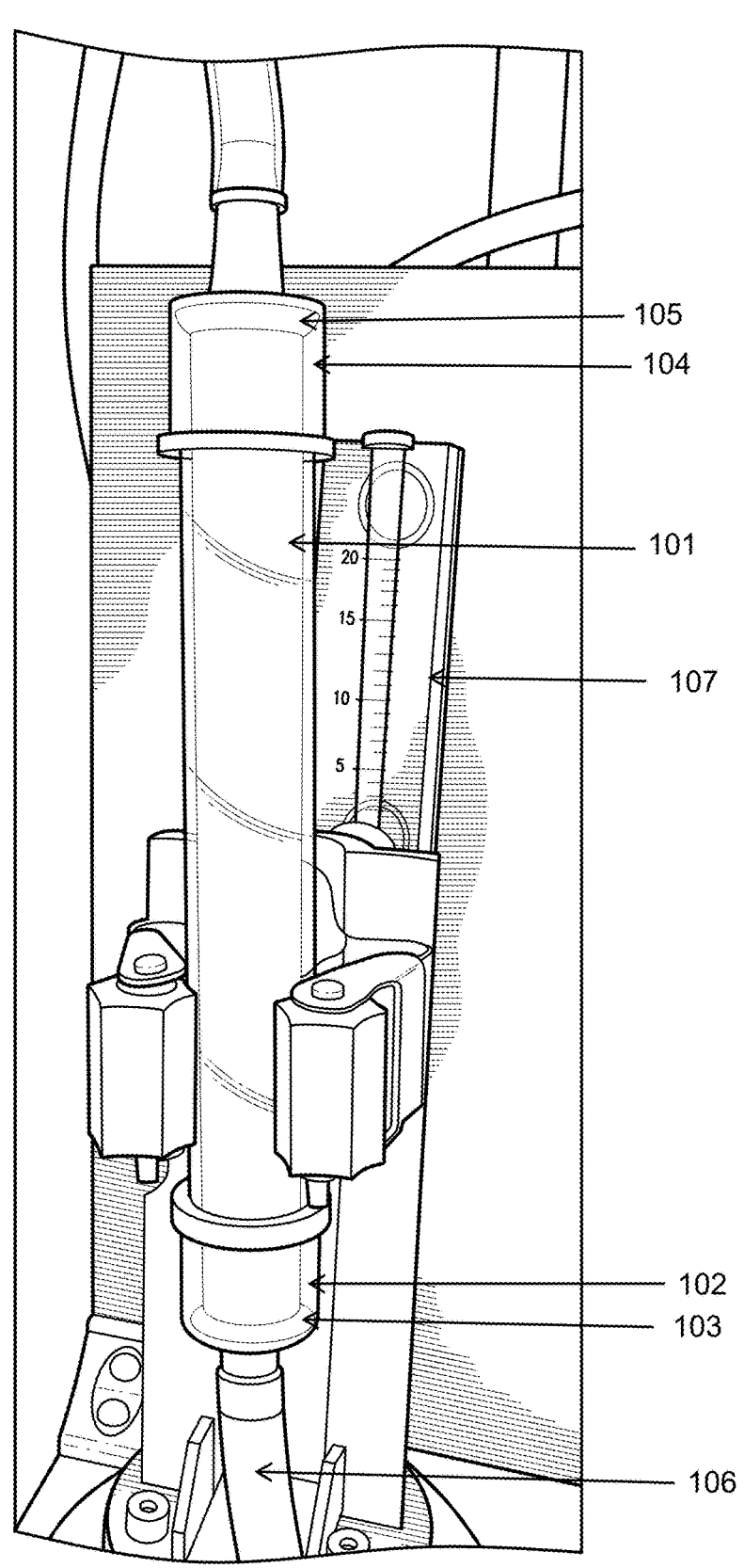
FIG. 1 shows a frontal view of one embodiment of a system of the present disclosure comprising a chamber, which comprises an inlet and an outlet, and a source for a drying gas. Measurements to provide information regarding the moisture content of pollen are obtained by either an instrument, which measures the humidity of the drying gas as it exits the outlet, or by a sensor, which directly measures the moisture content of the pollen in the chamber.

Modern plant breeding relies on outcrossing or cross-pollination to generate progeny plants having specific heritable traits. Such breeding strategies play an important role in F1 population development and trait integration. Corn (*Zea mays*), rice (*Oryza sativa*), wheat (*Triticum aestivum*), and sorghum (*Sorghum bicolor*), which belong to the Poaceae family and the Liliopsida class (monocots) of plants, are examples of economically important agricultural crops in which breeding has been hampered by low efficiency procedures in controlled cross-pollination. Further, in plants that exhibit hybrid vigor (heterosis), such as corn, commercial seed sold to farmers is typically F1 hybrid seed, and therefore such limitations not only impact development of new varieties during plant breeding, but also hamper efforts to produce seed for use by farmers in sufficient quantities and in an economical manner Pollen of plants from the Poaceae family is classified as recalcitrant or desiccation sensitive as described in Pacini and Dolferus, *Frontiers in Plant Sci.* 10:679; 2019. Other non-limiting examples of recalcitrant pollen include pollen of certain species in the Alismataceae, Amaranthaceae, Cactaceae, Chenopodiaceae, Cucurbitaceae, Anacardiaceae, Portulacaceae, Urticaceae, Lauraceae, Liliaceae, Iridaceae, Orchidaceae, Acanthaceae, and Caryophyllaceae families (Pacini and Dolferus, 2019). Conventional methods for cross pollination of such species, for example corn, entails emasculation of female plants and interspersing rows of male parent plants. This process is inefficient as it depends on the effective flow of pollen to the female plants, which is vulnerable to wind and requires that the male and female plants enter the reproductive phase at the same time. Alternatively, hand pollination may be used, but is highly labor intensive.

Storage of pollen in a manner that maintains viability and fertility would allow for pollination that does not depend on active pollen shed, temporal synchrony with female flower receptivity, or the use of male sterility. Pollen viability often decreases rapidly once it is shed, and pollen from the Poaceae family of plants, such as corn (*Zea mays*), rice (*Oryza sativa*), wheat (*Triticum aestivum*), and sorghum (*Sorghum bicolor*), remains viable for a particularly short time period. Therefore, improved methods to maintain pollen viability and fertility during storage are needed and are of significant value to the agricultural industry.

Existing methods for drying recalcitrant or monocot pollen prior to cryopreservation do not provide reproducible results, which is especially problematic because excessive drying leads to irreversible desiccation damage to recalcitrant pollen (Barnabas, *Annals of Botany*, 55:201-204, 1985; Buitink, et al., *Plant Physiol.*, 111:235-242, 1996). This could lead to loss of critical genetic resources in crops with recalcitrant pollen, including particularly important crops such as corn. The problem has remained as successful cryopreservation requires on the one hand that enough moisture be removed to minimize the risk of ice formation during cooling, but also that enough moisture be retained such that the pollen is not irreversibly damaged prior to freezing.

The present invention provides a significant advancement in the art by providing systems and methods that measure or predict pollen moisture content in real-time during drying, thus permitting reproducible, successful drying of pollen to a desired moisture content. This provides a reproducible means for achieving a pollen moisture content that is suitable for cryopreservation, and thus a reliable means of storing pollen that maintains pollen viability and fertility that has not been feasible prior to the present disclosure. The systems and methods of the present disclosure also provide a reliable means for achieving a pollen moisture content that is suitable for short-term pollen storage. The achievement of a reliable means for long-term pollen storage allows for subsequent use of the pollen in breeding programs or for field seed production, thereby preserving important genetic resources that might otherwise be lost. Successful long-term storage would allow breeders to conduct crosses between parents grown at different times and in different regions, which would significantly improve workflow and expand progeny diversity. Hybrid seed production may also benefit from the availability of long-term stored pollen by allowing for an increased number of female plants to be planted in a field, resulting in increased yield.

The current invention thus may be used to eliminate the need for in-field synchronized male and female plant development, also minimizing the effects of variable weather conditions. The present disclosure therefore permits implementation of high-throughput methods for the delivery of stored donor pollen to a recipient female reproductive part of a plant. The methods provided herein may, in some embodiments, substantially reduce the time and labor previously required to facilitate plant cross-pollination. In other embodiments, the methods provided herein may substantially improve the logistics and efficiency of plant cross-pollination. This is of particular significance as modern plant breeding programs may require tens of thousands or even hundreds of thousands of individual crosses or more on a yearly basis in order to produce new plant varieties with improved traits.

Systems and Methods for Drying Pollen

The present disclosure provides an integrated system for drying pollen prior to cryopreservation that includes a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and either a) an instrument in fluid communication with the outlet configured to measure the humidity of the drying gas that enters the outlet; or b) a sensor configured to obtain at least one moisture content measurement of the pollen within the chamber. "Chamber" as used herein refers to any enclosed vessel capable of containing pollen and receiving a drying gas to permit drying of the pollen when contacted with the gas. The chamber may be any appropriate geometrical shape, non-limiting examples of which include a cylinder, a sphere, a triangular prism, a cube, and a conical frustrum. "Drying gas" as used herein refers to any low moisture gas suitable for contacting pollen within in order to remove moisture from the pollen. Drying gases may include, but are not limited to, air, nitrogen, oxygen, argon, and helium.

As used herein an "instrument configured to measure humidity" refers to an instrument capable of measuring the amount of moisture in a gas. Non-limiting examples of such instruments include a hygrometer, a chilled-mirror dewpoint sensor, a psychrometer, and a capacitance-based humidity sensor. In some embodiments, the sensor may be in direct contact with the pollen in the chamber. In other embodiments, the sensor is in sufficient proximity to the chamber to obtain at least one moisture content measurement but is not in direct contact with the pollen within the chamber. In a particular embodiments, the pollen is not retained within the chamber. In one embodiment, the sensor may be configured to obtain at least one moisture content measurement of pollen that is not retained within the chamber. The sensor may for example be in direct contact with or in sufficient proximity to pollen that is not retained within the chamber to obtain at least one moisture content measurement of pollen. Non-limiting examples of sensors that can be used in a system of the present invention include a near infrared sensor, a nuclear magnetic resonance sensor, a microwave sensor, or a capacitance sensor.

In one embodiment, the inlet comprises a first filter or the outlet comprises a second filter, wherein the first or second filter is permeable to the drying gas and impermeable to the pollen. In another embodiment, the first filter or the second filter has a pore diameter of less than about 150 μm, 140 μm, 130 μm, 120 μm, 110 μm, 100 μm, 90 μm, 80 μm, 70 μm, 60 μm, 50 μm, 40 μm, 30 μm, 20 μm, or 10 μm, including all ranges derivable therebetween. Any filter having a pore diameter which allows the drying gas to pass from the inlet through the chamber to the outlet while retaining the pollen inside the chamber may be used. Plant pollen may range in size from about 5 μm to about 200 μm in diameter. Corn pollen for example may have a diameter of about 60 μm to about 120 μm. Rice pollen for example may have a diameter of about 20 μm to about 50 μm.

In one embodiment, the instrument or sensor is in electronic communication with a display unit capable of displaying the humidity or moisture content measurement. In another embodiment, the instrument or sensor is in electronic communication with a processor configured to determine when the pollen has reached a desired moisture content. In yet another embodiment, the processor is in electronic communication with an automated switch configured to stop the flow of the drying gas when the desired moisture content has been reached. In still yet another embodiment, the desired moisture content is a wet basis moisture content between about 10% and about 35%. The "wet basis moisture content" as used herein refers to the percentage equivalent of the ratio of the weight of water to the total weight of the pollen. The desired wet basis content measurement may be for example about 10%, 15%, 20%, 25%, 30%, or 35%, including all ranges derivable therebetween. In one embodiment, the desired moisture content is a dry basis moisture content between about 17% and about 55%. The "dry basis moisture content" as used herein refers to percentage equivalent of the ratio of the weight of water to the dry weight of the pollen. In another embodiment, the desired dry basis moisture content is between about 17.6% and about 53.8%. The desired dry basis moisture content may be for example about 17%, 20%, 25%, 30%, 35%, 40%, 45%, 50%, or 55%, including all ranges derivable therebetween. In one embodiment, the system comprises a controller configured to regulate the flow of the drying gas into the chamber. Non-limiting examples of controllers include a differential pressure mass flow controller, a thermal mass flow controller, and a Coriolis mass flow controller. In another embodiment, the processor in is electronic communication with the controller configured to regulate the flow of the drying gas into the chamber. In yet another embodiment, the system comprises a second instrument in fluid communication with the inlet configured to obtain at least one humidity measurement of the drying gas. In still yet another embodiment, the second instrument is in electronic communication with a display unit capable of displaying the humidity measurement. In one embodiment, the second instrument is in electronic communication with a processor configured to determine when the pollen has reached a desired moisture content. In another embodiment, the system further comprises a first thermometer in fluid communication with the outlet configured to measure the temperature of the drying gas that enters the outlet or a second thermometer in fluid communication with the inlet configured to measure the temperature of the drying gas that enters the inlet. In yet another embodiment, the first and/or the second thermometer is in electronic communication with a display unit capable of displaying the humidity measurement. In still yet another embodiment, the first and/or second thermometer is in electronic communication with a processor configured to determine when the pollen has reached a desired moisture content.

In another aspect, the present disclosure provides a system for drying pollen comprising: a sensor configured to obtain at least one moisture content measurement of the pollen during the drying, wherein the sensor is in electronic communication with a processor configured to determine when the pollen has reached a desired moisture content. In one embodiment, the sensor is configured to obtain a plurality of moisture content measurements. In another embodiment, the sensor is in electronic communication with a display unit capable of displaying the moisture content measurement. In yet another embodiment, the at least one moisture content measurement is a wet basis moisture content measurement. In still yet another embodiment, the at least one moisture content measurement is a dry basis moisture content measurement. Non-limiting examples of sensors that may be utilized in the present invention include a near infrared sensor, a nuclear magnetic resonance sensor, a microwave sensor, or a capacitance sensor. The drying may be performed using any method known in the art, including but not limited, to exposing pollen to ambient conditions for a sufficient time period to dry the pollen. In one embodiment, the desired moisture content is a wet basis moisture content between about 10% and about 35%. In another embodiment, the desired moisture content is a dry basis moisture content between about 17% and about 55%. A sensor of the present invention, when used to measure pollen moisture content throughout any drying process, allows pollen to be reproducibly dried to a desired moisture content. In some embodiments, the desired moisture content may be a moisture content, higher than the moisture content at which removal of "non-freezing" water begins. Drying to such a desired moisture content may be desired to prevent ice crystal formation and decrease mechanical stress, thus preserving pollen viability and fertility following storage. The moisture content at which the removal of "non-freezing" water begins may be determined empirically using the methods described herein.

The term "about" is used to indicate that a value includes the standard deviation of the mean for the device or method being employed to determine the value. As used herein, "pollen" refers to at least one pollen grain and may comprise a plurality of pollen grains. Non-limiting examples of pollen that may be used according to the system and methods of the invention include recalcitrant pollen, pollen collected from a dicot plant, a monocot plant, a cereal plant, a Poaceae family plant, an Alismataceae family plant, an Amaranthaceae family plant, a Cactaceae family plant, a Chenopodiaceae family plant, a Cucurbitaceae family plant, a Anacardiaceae family plant, a Portulacaceae family plant, a Urticaceae family plant, a Lauraceae family plant, a Liliaceae family plant, a Iridaceae family plant, a Orchidaceae family plant, a Acanthaceae family plant, a Caryophyllaceae family plant, a corn plant, a rice plant, a wheat plant, a sorghum plant, or a canola plant. As used herein "recalcitrant pollen" refers to desiccation sensitive pollen as described in Pacini and Dolferus (*Frontiers in Plant Sci.* 10:679; 2019). As used herein a "cereal plant" refers to a grass plant cultivated for the edible components of its grain. Non-limiting examples of cereal plants include corn, rice, wheat, and sorghum plants. Pollen for use in the present invention includes pollen collected from virtually any plant. In specific embodiments, the pollen may be derived from a plant which is diploid, double haploid, or transformed. In one embodiment, the pollen may be collected from a $T_0$ transformed plant. Pollen for use in the present invention may be obtained using any manual or automated methods well known in the art. In certain embodiments, pollen may be fresh, may be dried or partially dried, or may be stored for a short time at high humidity and low temperature prior to being added to the system.

The embodiments of the disclosure described herein are not intended to be exhaustive or to limit the disclosure to the precise forms disclosed. Instead, the embodiments selected for description have been chosen to enable one skilled in the art to practice the invention. It should be understood that the concepts presented herein may be used in various applications and should not be limited to use in the specific embodiments depicted in the drawings.

FIG. 1 is a diagram showing a system having a chamber 101 comprising an inlet 102 comprising a first filter 103, an outlet 104 comprising a second filter 105, a source for a drying gas 106 in fluid communication with the inlet 102, and an airflow meter 107 in fluid communication with the inlet 102. In certain aspects, the system comprises an instrument in fluid communication with the outlet 104 that is configured to obtain at least one humidity measurement of the drying gas as it enters the outlet 104. In other aspects, the system comprises a sensor configured to obtain at least one moisture content measurement of the pollen within chamber 101.

Figure 2:
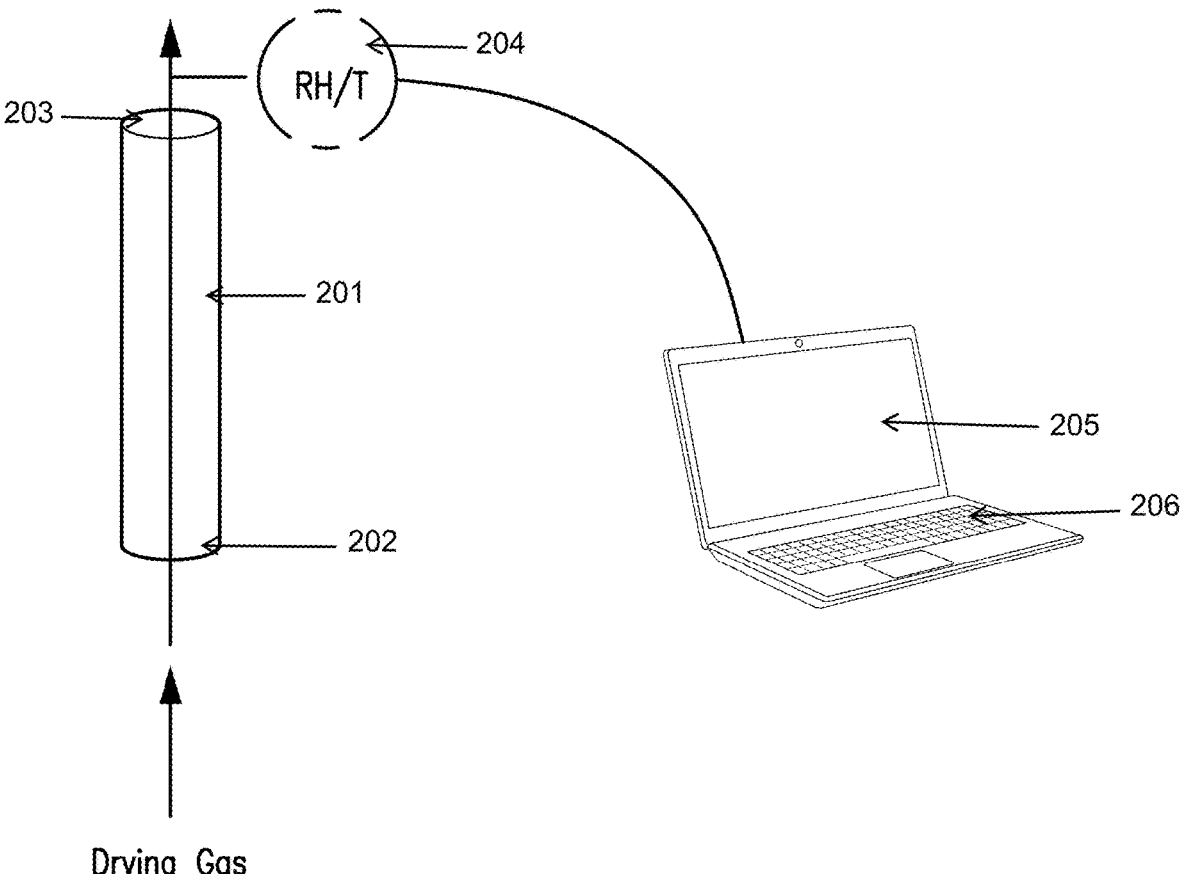
FIG. 2 shows a diagram of one embodiment of a system of the present disclosure in which the instrument is in electronic communication with a display unit and with a processor.

FIG. 2 is diagram showing a system having a chamber 201 comprising an inlet 202, an outlet 203, an instrument 204 in fluid communication with the outlet 203 configured to obtain at least one humidity measurement and at least one temperature measurement of the drying gas as it enters the outlet 203, a display unit 205 in electronic communication with the instrument 204, and a processor 206 in electronic communication with the instrument 204.

Figure 3:
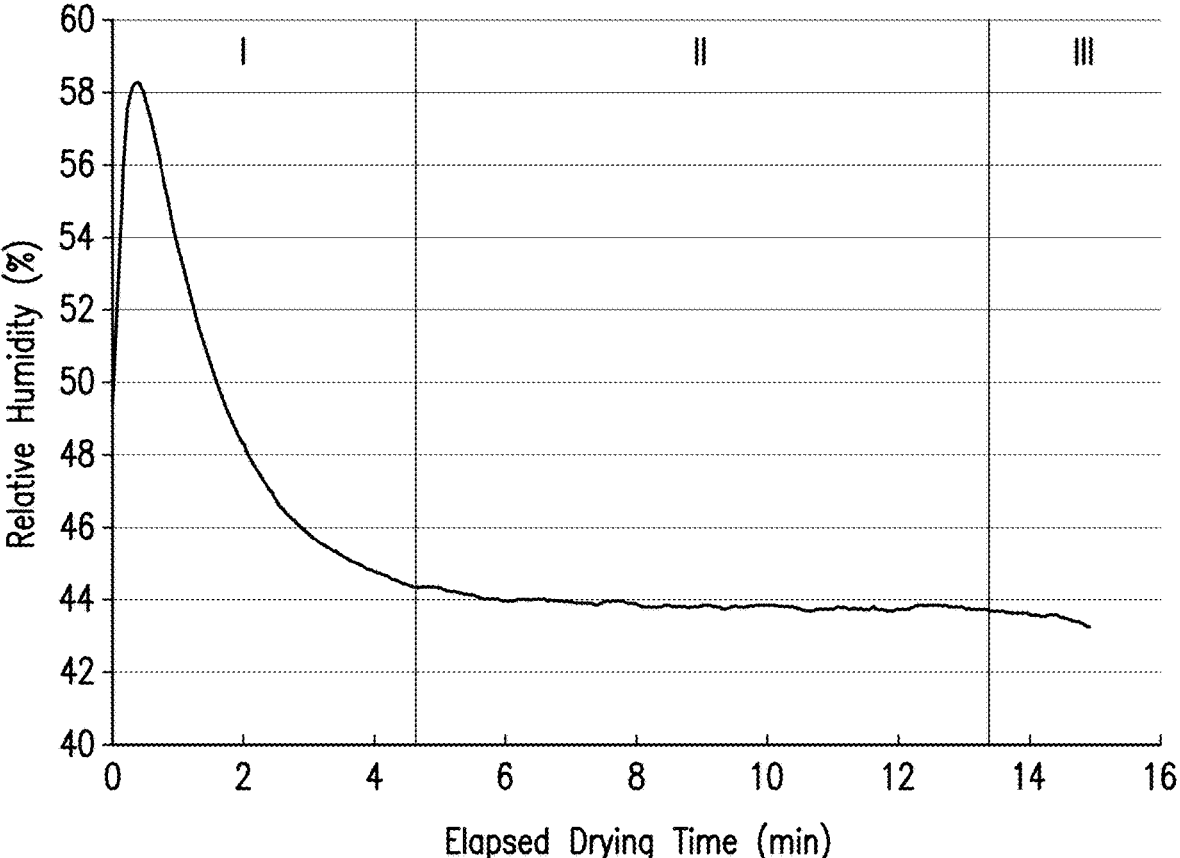
FIG. 3 shows a representative plot of the relative humidity of a drying gas as it exits a system of the present disclosure versus elapsed drying time for pollen exhibiting a characteristic drying curve. The transition from the constant rate (II) to falling rate (III) drying period approximately corresponds to the maximum moisture content at which pollen can be cryopreserved using practical cooling and warming rates.

FIG. 3 shows a representative plot of the relative humidity of a drying gas as it exits a system of the present invention versus elapsed drying time for pollen exhibiting a characteristic drying curve. A characteristic drying curve may be obtained when the drying gas is of a sufficiently low humidity, and the drying gas inlet composition, flow rate, and temperature are held constant. The drying gas may for example have a relative humidity of about 0% to about 95%, of about 0% to about 50%, of about 0% to about 25%, of about 0% to about 15%, of about 0% to about 10%, or of about 0% to about 5%. It may be desired in some embodiments to use a drying gas with a relative humidity of about 0%. Lower humidity drying gases reduce the drying time required to dry pollen to a desired moisture content, which improves efficiency and maintains high pollen viability and fertility. The characteristic drying curve illustrated in FIG. 3 can be visually segmented into three distinct regions each with different drying kinetics. Region I represents the induction period in which readily available moisture at the surface of the pollen is quickly volatilized and removed and the temperature of the pollen bed is high. As drying continues, the temperature of the pollen decreases due to evaporative cooling, ultimately reaching a steady state. Region II represents the constant rate drying period in which diffusion of moisture from the interior of the pollen grain occurs at a rate sufficient to maintain surface moisture at a constant level. Region III represents the falling rate period which occurs once diffusion of internal moisture begins to slow. The transition from the constant rate (Region II) to (Region III) falling rate drying period approximately corresponds to the maximum moisture content at which pollen can be successfully cryopreserved with practical cooling and warming rates. In one embodiment, the Region II to Region III transition can be obtained by calculating the slope of the change in the moisture content of drying gas from the outlet.

Figure 4:
FIG. 4 shows seed set obtained by pollinating with corn pollen dried and stored using the systems and methods of the present disclosure.

As an illustrative example, corn pollen dried to the Region II to Region III transition using a system of the present invention, cryopreserved in liquid nitrogen at −196° C., and stored for 4 hours is able to produce full seed set as shown in FIG. 4. Full seed has also been achieved using corn pollen dried according to the systems and methods of the present invention, cryopreserved in liquid nitrogen at −196° C. and stored for up to 1 year.

Figure 5:
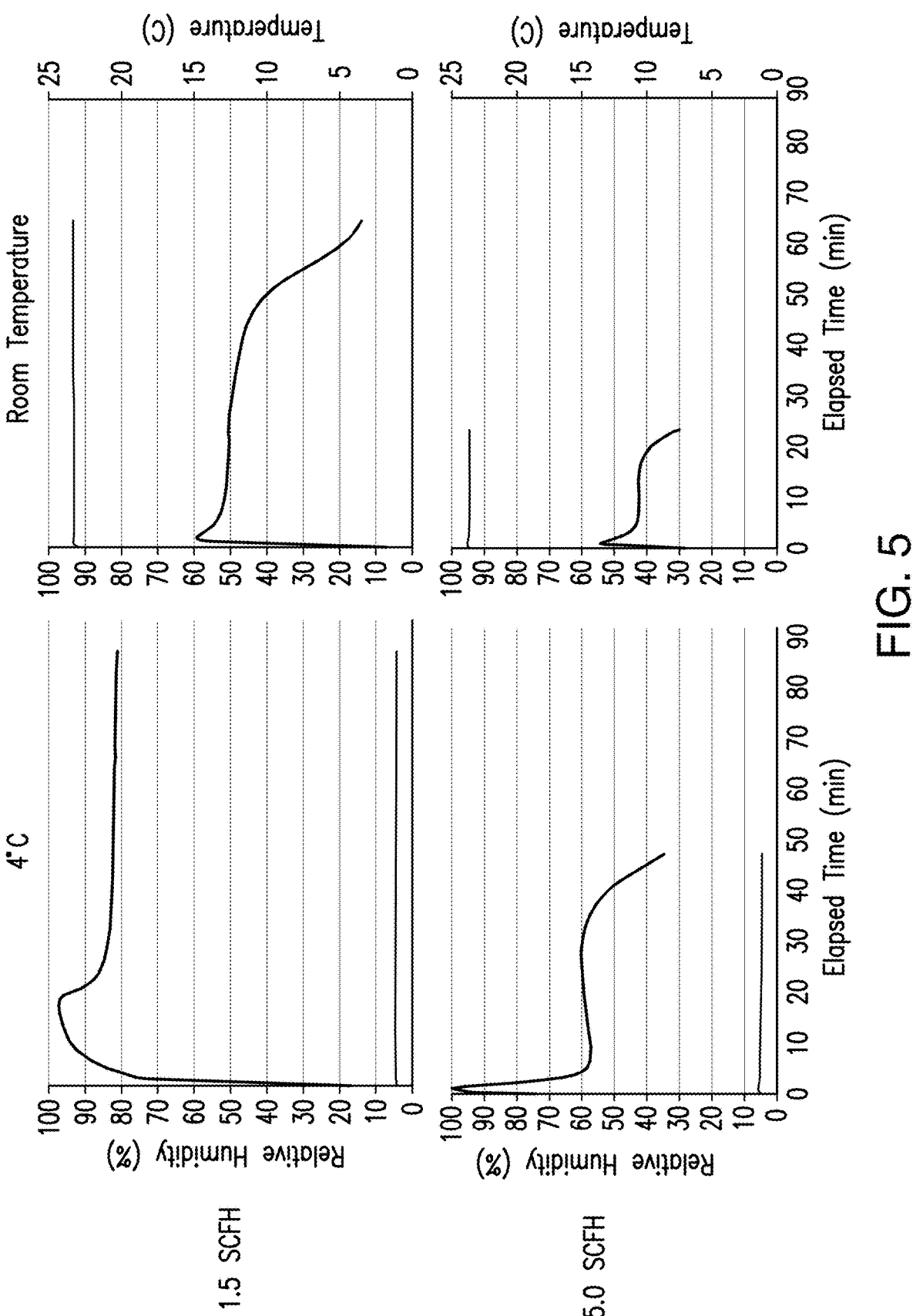
FIG. 5 shows that the temperature and flow rate of the drying gas impact the drying time required to achieve a desired moisture content.

FIG. 5 illustrates that the temperature and flow rate of the drying gas impact the drying time required achieve a desired moisture content, however, the transition from the constant rate (Region II) to falling rate (Region III) drying period continues to approximate the maximum moisture content at which pollen can be successfully cryopreserved with practical cooling and warming rates.

Figure 6:
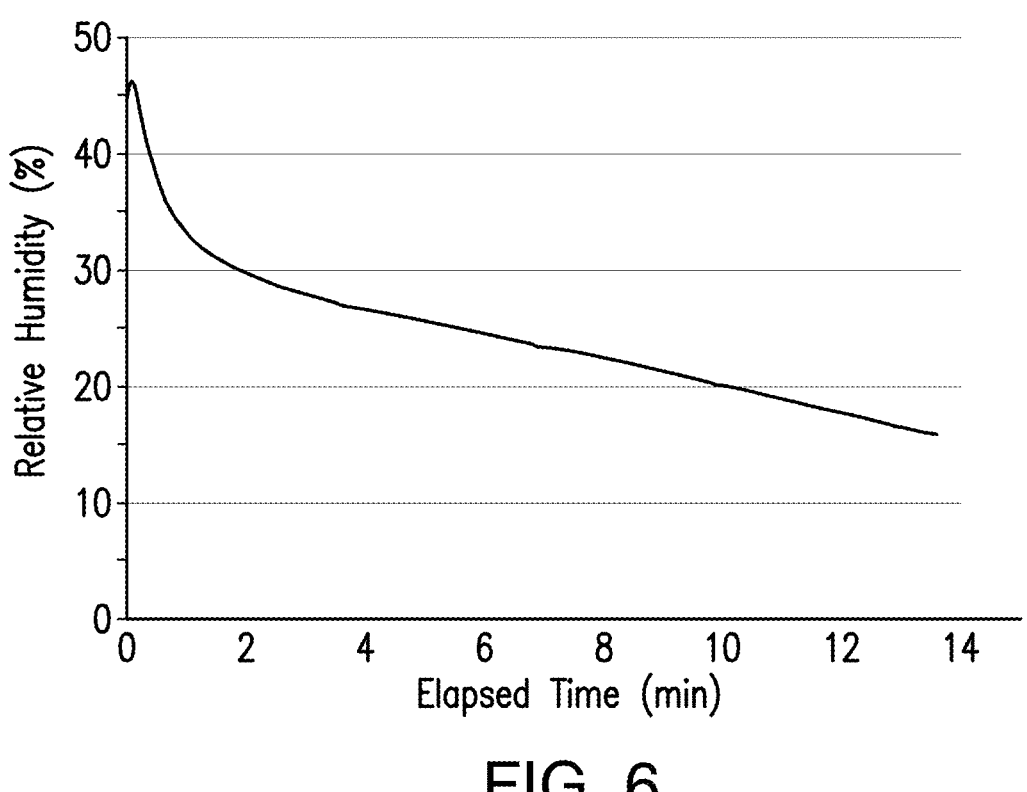
FIG. 6 shows a representative plot of the relative humidity of a drying gas as it exits a system of the present disclosure versus elapsed time for pollen exhibiting a non-characteristic drying curve. The transition from the constant rate to the falling rate drying period is not pronounced in pollen exhibiting a non-characteristic drying curve.

FIG. 6 illustrates a representative plot of the relative humidity of a drying gas as it exits a system versus elapsed time for pollen exhibiting a non-characteristic drying curve. The transition from the constant rate (Region II) to the falling rate (Region Ill) drying period is not pronounced in pollen exhibiting a non-characteristic drying curve. Since the Region II to Region III transition is not pronounced, pollen which exhibits a non-characteristic drying curve is at increased risk of irreversible desiccation damage during drying if the transition point is used as the indicator to stop the flow of the drying gas into the chamber.

Figure 7:
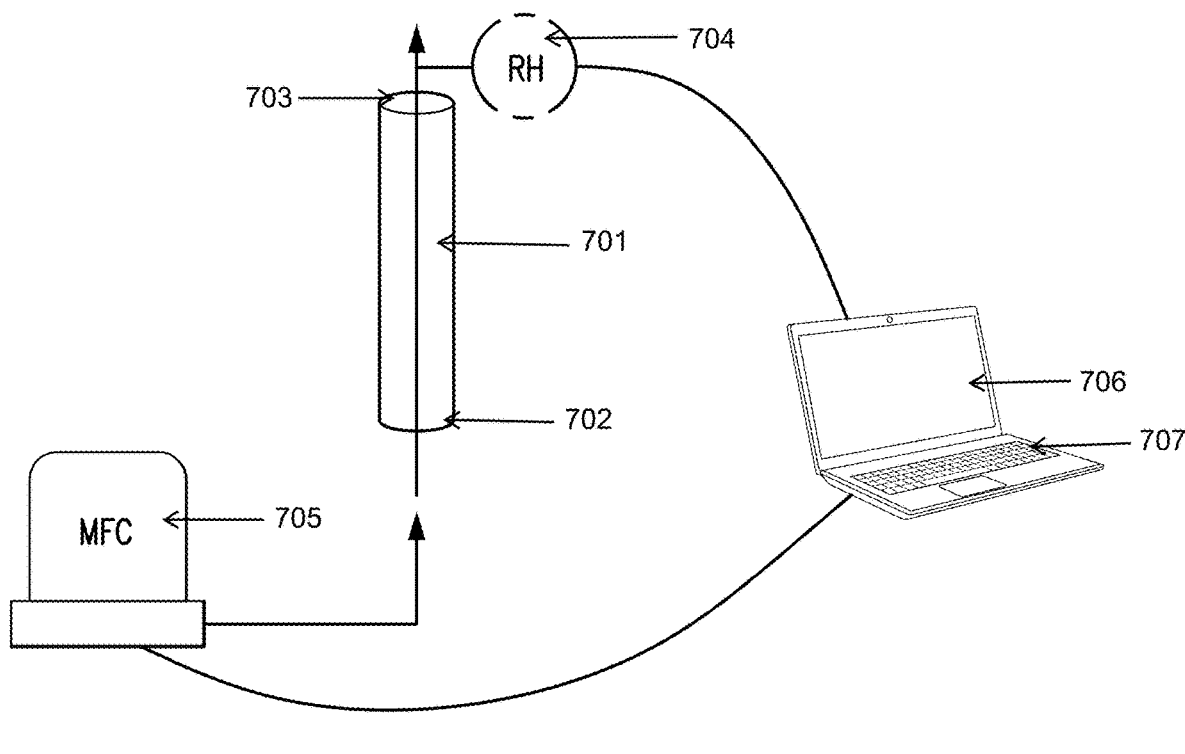
FIG. 7 shows a diagram of one embodiment of a system of the present disclosure in which the system comprises a controller and the instrument of the system is in electronic communication with a display unit and a processor and the processor is in electronic communication with the controller.
Figure 8:
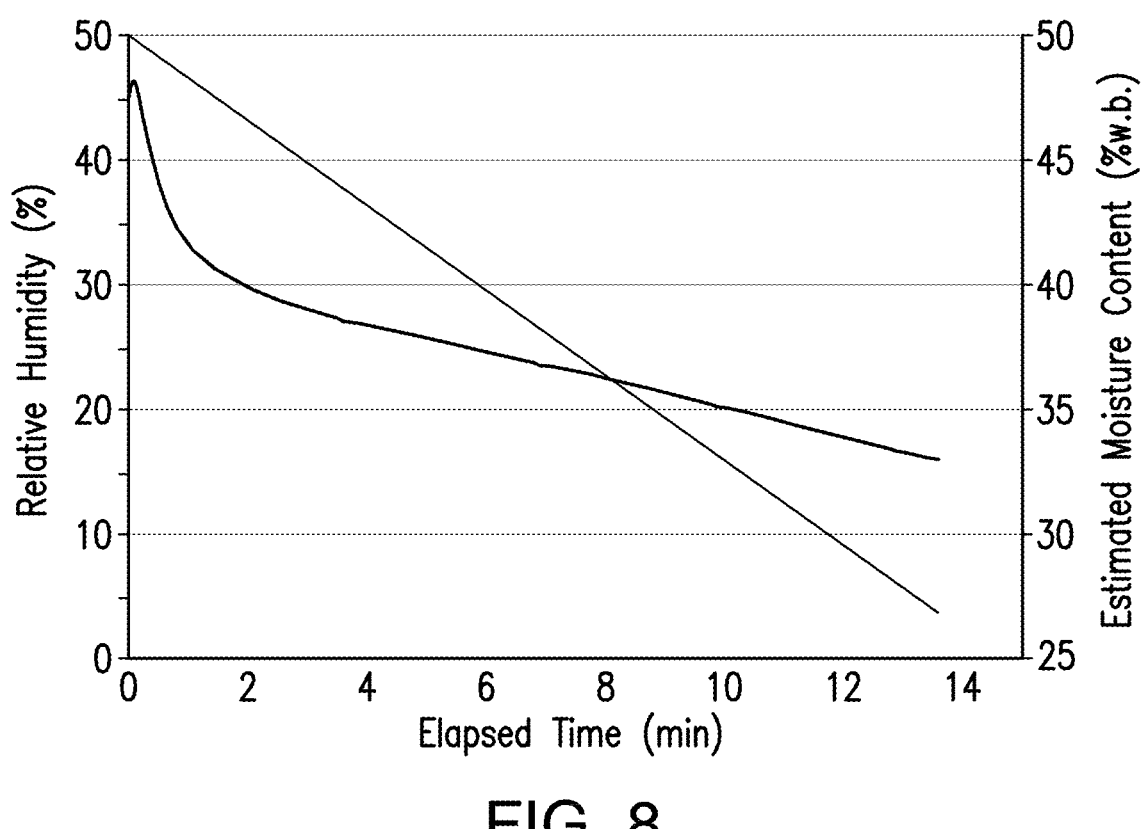
FIG. 8 shows a representative plot of the continuous approximation of pollen moisture content using the system of the present disclosure.
Figure 11:
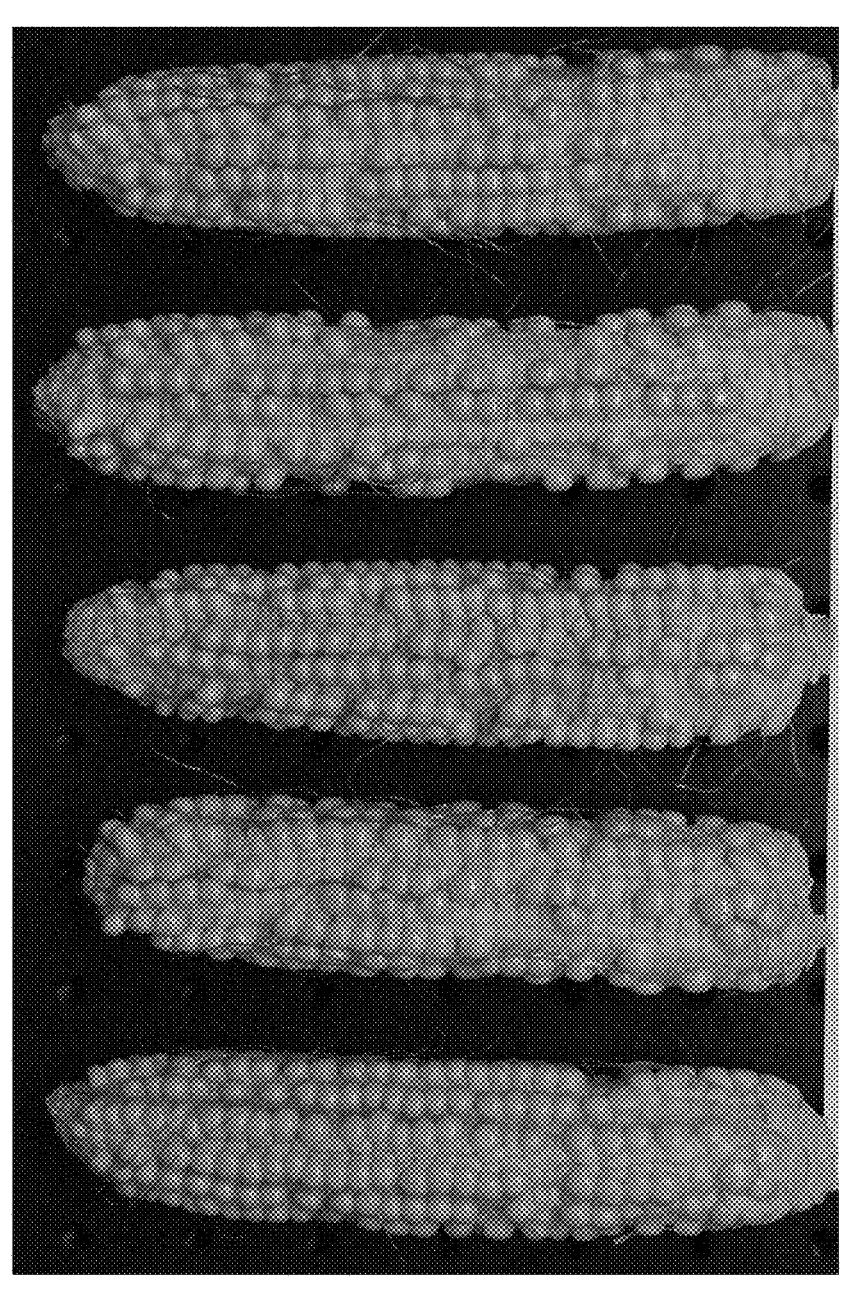
FIG. 11 shows seed set obtained by pollinating with corn pollen dried and stored using the systems and methods of the present disclosure.

FIG. 7 is a diagram of a system having a chamber 701 comprising an inlet 702, an outlet 703, an instrument 704 in fluid communication with the outlet 703, a controller 705, a display unit 706 in electronic communication with the instrument 704, and a processor 707 in electronic communication with the instrument 704 and the controller 705. The instrument 704 is configured to obtain at least one humidity measurement, at least one pressure measurement, and at least one temperature measurement of the drying gas as it enters the outlet 703. The controller 705 is configured to precisely regulate the flow of the drying gas into the chamber 701. The controller is used in combination with the instrument to enable the calculation of the mass flow rate of water exiting the system. When the initial weight and moisture content of the pollen in the chamber is known, the continuous approximation of moisture content throughout the drying process can be calculated by performing a water mass balance. FIG. 8 illustrates a representative plot of the continuous approximation of pollen moisture content using the system described in FIG. 7. In certain aspects, the controller of the present invention may be replaced by a mass flow meter which measures the flow rate of the drying gas as it enters the chamber through the inlet. Seed set obtained following pollination with corn pollen dried using the system described in FIG. 7 and cryopreserved is shown in FIG. 11.

Figure 9:
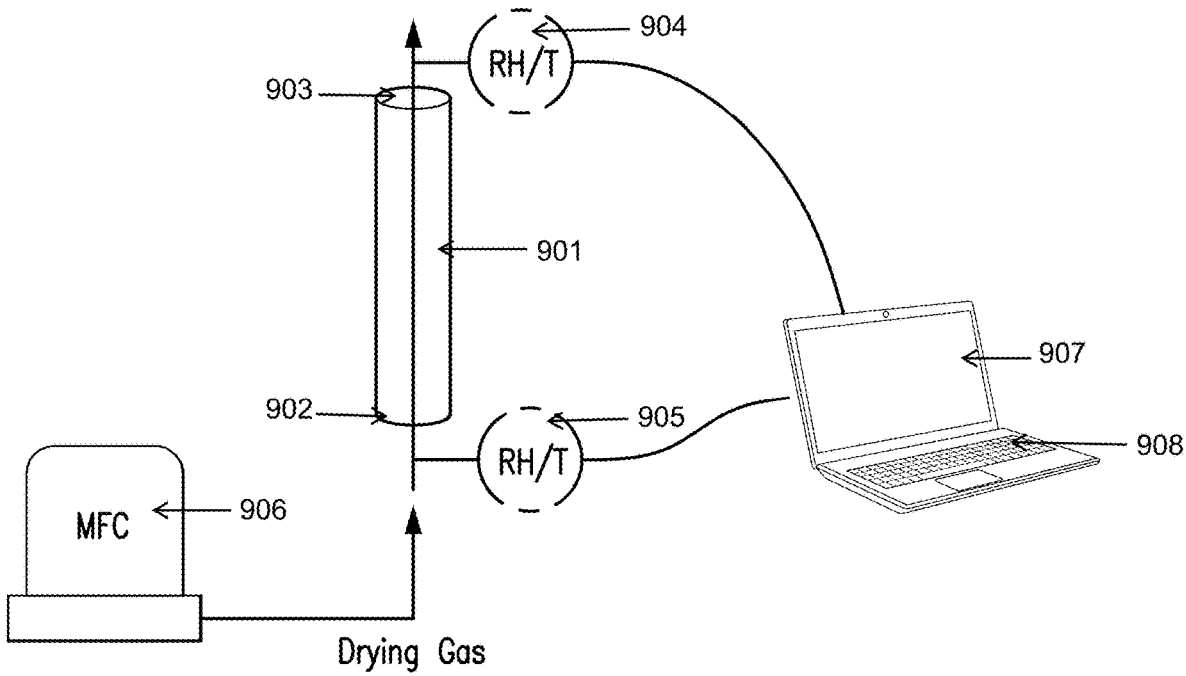
FIG. 9 shows a diagram of one embodiment of the of the present disclosure in which the system comprises a second instrument to measure the humidity of the drying gas as it enters the inlet. The second instrument is in electronic communication with a display unit and with a processor.

FIG. 9 is a diagram of a system having a chamber 901 comprising an inlet 902, an outlet 903, an first instrument 904 in fluid communication with the outlet 903, a second instrument 905 in fluid communication with the inlet 902, a controller 906, a display unit 907 in electronic communication with the first instrument 904 and the second instrument 906, and a processor 908 in electronic communication with the first instrument 904, the second instrument 905, and the controller 906. The first instrument 904 is configured to obtain at least one humidity measurement, at least one pressure measurement, and at least one temperature measurement of the drying gas as it enters the outlet 903, the second instrument 905 is configured to obtain at least one humidity measurement and at least one temperature measurement of the drying gas as it enters the inlet 902. The controller 906 is configured to precisely regulate the flow of the drying gas into the chamber 901. The controller is used in combination with the first instrument and the second instrument to enable the calculation of the mass flow rate of water exiting the system in situations where the drying gas contains more than trace levels of moisture. It may be desired for example to use the second instrument to obtain at least one humidity measurement and at least one temperature measurement of the drying gas as it enters the inlet when the drying gas has a relative humidity greater than about 0%. In some embodiments, the second instrument may be used to obtain at least one humidity measurement and at least one temperature measurement of the drying gas as it enters the inlet to confirm that the drying gas has a relative humidity of about 0%. When the initial weight and moisture content of the pollen in the chamber is known, the continuous approximation of moisture content throughout the drying process can be calculated by performing a mass water balance. In certain aspects, the controller of the present invention may be replaced by a mass flow meter which measures the flow rate of the drying gas as it enters the chamber through the inlet, but does not directly control the flow rate. In specific embodiments, the mass flow meter may be positioned at the inlet end or the outlet end of the drying system. In one embodiment, the mass flow meter may preferably be positioned at the inlet end of the drying system.

Figure 10:
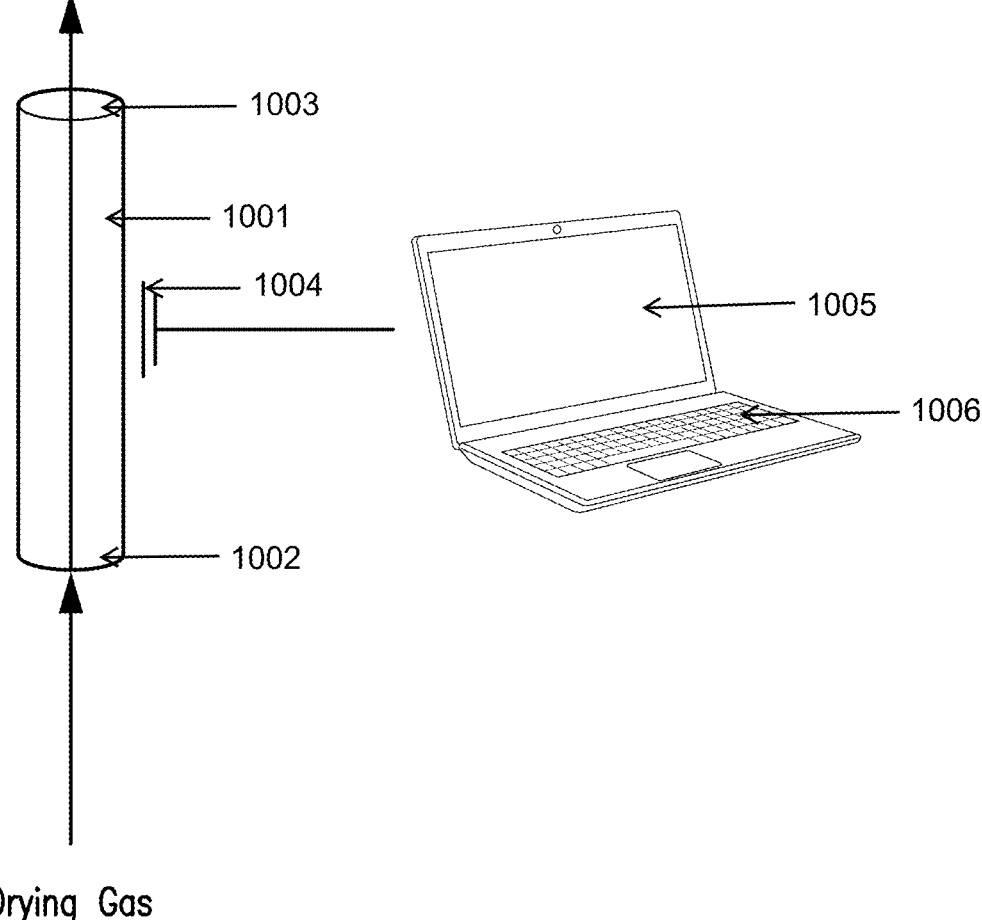
FIG. 10 shows a diagram of one embodiment of the present disclosure in which the sensor is in electronic communication with a display unit.

FIG. 10 is diagram showing a system having a chamber 1001 comprising an inlet 1002, an outlet 1003, a sensor 1004 configured to obtain at least one moisture content measurement of the pollen within the chamber 1001, a display unit 1005 in electronic communication with the sensor 1004, and a processor 1006 in electronic communication with the sensor 1004. In certain aspects, the sensor is in direct contact with the pollen within the chamber. In other aspects, the sensor is in sufficient proximity to the chamber to obtain at least one moisture content measurement but is not in direct contact with the pollen within the chamber.

In another aspect, a method for drying pollen is provided herein comprising drying the pollen using a system of the invention. In one embodiment, the system comprises a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and an instrument in fluid communication with the outlet configured to measure the humidity of the drying gas that enters the outlet. In another embodiment, the system comprises a chamber for drying pollen, the chamber comprising an inlet and an outlet and being configured to permit a drying gas to contact pollen retained within the chamber when the drying gas passes from the inlet through the chamber to the outlet; a source for the drying gas in fluid communication with the inlet; and a sensor configured to obtain at least one moisture content measurement of the pollen within the chamber. In some embodiments, the conditions of the drying method may be optimized for a particular application or particular pollen type. Such parameters can be determined empirically using the methodology described herein. To promote cross-pollination, for example, it may be desired to use a pollen with a moisture content that facilitates cryopreservation, maintains high viability of the pollen grains, and which does not significantly hinder fertilization and seed development following drying. It is critical for example to ensure that enough moisture is removed during the drying process to minimize the risk of ice formation during cooling, but also that enough moisture be retained such that the pollen is not irreversibly damaged prior to cryopreservation. Non-limiting examples of pollen that may be used according to the systems and methods of the invention include recalcitrant pollen, pollen collected from dicot plant, a monocot plant, a cereal plant, a Poaceae family plant, an Alismataceae family plant, an Amaranthaceae family plant, a Cactaceae family plant, a Chenopodiaceae family plant, a Cucurbitaceae family plant, a Anacardiaceae family plant, a Portulacaceae family plant, a Urticaceae family plant, a Lauraceae family plant, a Liliaceae family plant, a Iridaceae family plant, a Orchidaceae family plant, a Acanthaceae family plant, a Caryophyllaceae family plant, a corn plant, a rice plant, a wheat plant, a sorghum plant, or a canola plant.

In one embodiment, the method comprises obtaining at least one measurement that provides information regarding the moisture content of the pollen in the chamber. In another embodiment, the method comprises determining when the pollen has reached a desired moisture content. The determining may comprise for example calculating the slope of the change in the moisture content of drying gas from the outlet and may in some embodiments be performed by a processor in electronic communication with the instrument or the sensor. In another embodiment, the method comprises stopping the flow of the drying gas into the chamber when the desired moisture content has been reached. In some embodiments, the stopping may be automated. In still yet another embodiment, the method comprises collecting pollen from the chamber following the drying.

In yet another aspect, a method for drying pollen is provided herein comprising: a) drying pollen; b) obtaining at least one measurement that provides information regarding the moisture content of the pollen; and c) determining when the pollen has reached a desired moisture content. Drying may be performed using any method known in the art, including but not limited, to exposing pollen to ambient conditions for a sufficient time period to dry the pollen. In one embodiment, the at least one measurement is obtained using a sensor. The sensor may be for example a near infrared sensor, a nuclear magnetic resonance sensor, a microwave sensor, or a capacitance sensor. In another embodiment, the measurement is a wet basis moisture content measurement of the pollen. In yet another embodiment, the measurement is a dry basis moisture content measurement of the pollen. In still yet another embodiment, the drying of the pollen is stopped when the pollen has reached the desired moisture content. In one embodiment, the determining is performed by a processor in electronic communication with the sensor. In another embodiment, the desired moisture content is a wet basis moisture content between about 10% and about 35%. In another embodiment, the desired moisture content is a dry basis moisture content between about 17% and about 55%. In yet another embodiment, the method comprises transmitting an electronic signal in response to obtaining the at least one measurement.

In order to maintain pollen viability and fertility, pollen should be cooled and warmed at a rate that is rapid enough to prevent ice crystal formation and decrease mechanical stress when the sample transitions to or from the glass phase. This minimum rate will vary depending on pollen moisture content. The minimum cooling and warming rates required to prevent ice crystal formation and decrease mechanical stress can be determined empirically using the methods described herein. As used herein the term "glass phase" is used to refer to a phase where the intracellular contents of the pollen adopt an amorphous solid structure. In some embodiments, it may be desired to cool the pollen very rapidly. In one example, the pollen may be placed in a cryovial and submerged in liquid nitrogen, a process which produces a cooling rate of about −50° C./min. In another example, an alternate low-boiling point liquid may be utilized. Non-limiting examples of such low-boiling point liquid include liquid hydrogen, liquid neon, liquid oxygen, and liquid helium. In yet another example, the cooling rate may be further increased by placing the pollen in an alternate vessel prior to submerging in a low-boiling point liquid, a non-limiting example of which is a Mylar® bag. The pollen may be cooled at a rate of at least about −5° C./min, −10° C./min, −20° C./min, −40° C./min, −60° C./min, −80° C./min, −100° C./min, −200° C./min, −300° C./min, −400° C./min, −500° C./min, −600° C./min, −700° C./min, −800° C./min, −900° C./min, −1000° C./min, −1500° C./min, −2000° C./min, −2500° C./min, −3000° C./min, −3500° C./min, −4000° C./min, −4500° C./min, or −5000° C./min, including all ranges derivable therebetween. Any method of cooling known in the art which is capable of cooling at rate of at least about −10° C./min may be used in accordance with the present invention. Pollen may be warmed for example by removing a cryovial of cryopreserved pollen from liquid nitrogen and immediately pouring the pollen from the cryovial onto the stigma of a recipient plant at ambient greenhouse temperatures. In specific embodiments, the pollen may be warmed by removing a cryovial of cryopreserved pollen from liquid nitrogen; allowing the cryovial to equilibrate at ambient greenhouse temperatures for 30 seconds; and pouring the pollen from the cryovial onto the stigma of a recipient plant at ambient greenhouse temperatures. In other embodiments, the pollen may be warmed by removing a cryovial of cryopreserved pollen from liquid nitrogen; allowing the cryovial to equilibrate at ambient greenhouse temperatures for 10 seconds; tapping the vial to mix pollen; opening the cryovial 20 seconds after removing from liquid nitrogen; and pouring the pollen from the cryovial onto the stigma of a recipient plant at ambient greenhouse temperatures 30 seconds after removing from liquid nitrogen. The warming rate may be for example at least about 10° C./min, 20° C./min, 40° C./min, 60° C./min, 80° C./min, 100° C./min, 200° C./min, 300° C./min, 400° C./min, 500° C./min, 600° C./min, 700° C./min, 800° C./min, 900° C./min, 1000° C./min, 1500° C./min, 2000° C./min, 2500° C./min, 3000° C./min, 3500° C./min, 4000° C./min, 4500° C./min, or 5000° C./min, including all ranges derivable therebetween. Any method known in the art which is capable of warming at a rate of at least about 10° C./min may be used in accordance with the present invention.

Storing Plant Pollen

In another aspect, a method of storing pollen is provided here, the method comprising: (a) obtaining pollen according to the methods of drying the pollen using the systems of the invention described herein; and (b) storing the pollen. In some embodiments, the conditions of the storage method may be optimized for a particular application or particular pollen type. Such parameters can be determined empirically using the methodology described herein. To promote cross-pollination, for example, it may be desired to store pollen that has been dried to a moisture content and cooled at a rate that facilitates cryopreservation and maintains pollen viability and fertility following storage. It is critical for example to ensure that enough moisture is removed during the drying process to minimize the risk of ice formation during cooling, but also that enough moisture be retained such that the pollen is not irreversibly damaged prior to cryopreservation. It is also critical that the pollen is cooled at an appropriate cooling rate and stored at an appropriate temperature to maintain viability. In order to maintain pollen viability and fertility, pollen should be cooled at a rate that is rapid enough to prevent ice crystal formation when the sample transitions to the glass phase, this minimum rate will vary depending on pollen moisture content and may be empirically determined using the systems and methods described herein. The pollen may for example be cooled at a rate of at least about −10° C./min. In one example, the pollen may be placed in a cryovial and submerged in liquid nitrogen, a process which produces a cooling rate of about −50° C./min. In some embodiments, the practical cooling rate may be for example at least about −5° C./min, −10° C./min, −20° C./min, −40° C./min, −60° C./min, −80° C./min, −100° C./min, −200° C./min, −300° C./min, −400° C./min, −500° C./min, −600° C./min, −700° C./min, −800° C./min, −900° C./min, −1000° C./min, −1500° C./min, −2000° C./min, −2500° C./min, −3000° C./min, −3500° C./min, −4000° C./min, −4500° C./min, or −5000° C./min, including all ranges derivable therebetween. Any method of cooling known in the art which is capable of cooling at a similar rate may be used. Non-limiting examples of pollen that may be used according to the systems and methods of the invention include recalcitrant pollen, pollen collected from dicot plant, a monocot plant, a cereal plant, a Poaceae family plant, an Alismataceae family plant, an Amaranthaceae family plant, a Cactaceae family plant, a Chenopodiaceae family plant, a Cucurbitaceae family plant, a Anacardiaceae family plant, a Portulacaceae family plant, a Urticaceae family plant, a Lauraceae family plant, a Liliaceae family plant, a Iridaceae family plant, a Orchidaceae family plant, a Acanthaceae family plant, a Caryophyllaceae family plant, a corn plant, a rice plant, a wheat plant, a sorghum plant, or a canola plant.

In certain embodiments, storing may performed at a temperature between about −196° C. and about −60° C. or at a temperature between about −196° C. and about −70° C. The storage temperature may be, for example, about −196° C., −190° C., −180° C., −170° C., −160° C., −150° C., −140° C., −130° C., −120° C., −110° C., −100° C., −90° C., −80° C., −76° C., −75° C., −70° C., −65° C., or −60° C., including all ranges derivable therebetween. In a particular embodiment, the storage temperature less than about −60° C. In particular embodiments, it may be desired to store pollen at a temperature below the glass transition temperature. The glass transition temperature may be determined empirically using the methods described herein. In some embodiments, the storing is performed for up to about 1 year, 5 years, 10 years, 15 years, 20 years, 25 years, or 30 years, including all ranges derivable therebetween. In other embodiments, the storing may be performed for at least about 15 minutes, 1 hour, 12 hours, 1 day, 1 week, 1 month, 6 months, 1 year, 2 years, 5 years, or 7 years, including all ranges derivable therebetween. In one embodiment, the pollen is capable of germination following storing. Germination can be done with any amount of pollen. In yet another embodiment, at least about 5% of pollen grains remain capable of germination on a stigma following storing. In particular embodiments, at least about 0.1%, 0.5%, 1%, 2%, 3%, 4%, 5%, 6%, 7%, 8%, 9%, 10%, 11%, 12%, 13%, 14% 15%, 20%, 25%, or 50% of pollen grains remain capable of germination on the stigma following storing. Assays to determine percent germination on the stigma are routine in the art. As one example, pollen may be applied to the stigma, incubated, fixed, stained using aniline blue, and visualized using UV dark field (Sari Gorla, et al., *Theoretical and Applied Genetics,* 46:289-294; 1975), specifically incorporated herein by reference.

In particular embodiments, pollen dried to a desired moisture content, as described herein, may be stored short-term. In one embodiment, drying pollen to a desired moisture content, as described herein, may prevent pollen clumping and thus allow for short-term pollen storage without the addition of any storage additive. Short-term storage may be performed, for example, at about −4.0° C., −3.0° C., −2.0° C., −1.0° C., −0.5° C., 0° C., 1° C., 2° C., 3° C., 4° C., 5° C., 6° C., 7° C., 8° C., 9° C., or 10° C., or at about 80%, 81%, 82%, 83%, 84%, 85%, 86%, 87%, 88%, 89%, 90%, 91%, 92%, 93%, 94%, 95%, 96%, 97%, 98%, 99%, or 100% relative humidity, including all ranges derivable therebetween. In one embodiment, the pollen may be stored in humidity chamber. In another embodiment, the airflow rate in the humidity chamber is between about 5.0 liters/min (l/min) and about 20.0 l/min. The airflow rate, for example, may be about 5.0 l/min, 6.0 l/min, 7.0 l/min, 8.0 l/min, 9.0 l/min, 10.0 l/min, 11.0 l/min, 12.0 l/min, 13.0 l/min, 14.0 l/min, 15.0 l/min, 16.0 l/min, 17.0 l/min, 18.0 l/min, 19.0 l/min, or 20.0 l/min, including all ranges derivable therebetween. In another embodiment, the airflow rate is an airflow rate which is sufficient to maintain a humidity chamber at about 0.5° C. to about 10° C. and/or at about 90% to about 100% relative humidity. An airflow rate of about 5.0 l/min to about 20.0 l/min for example is sufficient to maintain the humidity chamber at about 0.5° C. to about 10° C. and at about 90% to about 100% relative humidity for pollen volumes ranging from 1 grain to about 45 liters, however, the airflow rate required may be greater as the volume of pollen increases. The airflow rate required to maintain a humidity chamber at about 0.5° C. to about 10° C. and about 90% to about 100% relative humidity for any pollen volume may be determined empirically using the methods described herein, and potentially any airflow rate could find use in accordance with the invention. In some embodiments, the storing is performed for up to about 14 days or for from about 1 day to about 7 days. The storing may be performed, for example, for about 1 second, 15 seconds, 30 seconds, 45 seconds, 1 minute, 5 minutes, 15 minutes, 30 minutes, 45 minutes, 1 hour, 2 hours, 4 hours, 6 hours, 8 hours, 10 hours, 12 hours, 14 hours, 16 hours, 18 hours, 20 hours, 22 hours, 1 day, 2 days, 3 days, 4 days, 5 days, 6 days, 7 days, 8 days, 9 days, 10 days, 11 days, 12 days, 13 days, or 14 days, including all ranges derivable therebetween.

In one aspect, a method for evaluating pollen viability is provided herein comprising: (a) obtaining pollen; (b) delivering the pollen to a female reproductive part of a recipient plant; (c) washing the female reproductive part of the recipient plant to remove non-adhered pollen; and (d) evaluating adherence of the pollen to the female reproductive part of the recipient plant. In one embodiment, the evaluating is quantitative. In another embodiment, the evaluating comprises counting the number of pollen grains adhered to the female reproductive part of the recipient plant. In still yet another embodiment, the adhered pollen is fixed to the female reproductive part of the recipient plant prior to step (d). Pollen from virtually any plant may be evaluated using the methods described herein. Non-limiting examples of which include plants with recalcitrant pollen, dicot plants, monocot plants, cereal plants, Poaceae family plants, Alismataceae family plants, Amaranthaceae family plants, Cactaceae family plants, Chenopodiaceae family plants, Cucurbitaceae family plants, Anacardiaceae family plants, Portulacaceae family plants, Urticaceae family plants, Lauraceae family plants, Liliaceae family plants, Iridaceae family plants, Orchidaceae family plants, Acanthaceae family plants, Caryophyllaceae family plants, corn plants, rice plants, wheat plants, sorghum plants, and canola plants.

Delivery of Stored Pollen for Pollination of Plants

The present invention surprisingly permits cross-pollination of potentially any flowering plant or grass using stored pollen. In one embodiment, a method for pollinating a plant is provided herein, the method comprising: (a) obtaining pollen according the methods of drying or storing pollen provided herein; and (b) pollinating the plant with the pollen. In some embodiments, the methods of the invention may be optimized for a particular application, particular plant species, or particular pollen type. Such parameters can be determined empirically using the methodology described herein. In particular embodiments, corn plants having a shorter silk length may produce a higher seed set compared to corn plants having a longer silk length. In certain embodiments, pollination at a higher and/or increasing relative humidity may produce a higher seed set compared to pollination at a lower or decreasing relative humidity. Non-limiting examples of plants that may be used according to the methods of the invention include plants with recalcitrant pollen, dicot plants, monocot plants, cereal plants, Poaceae family plants, Alismataceae family plants, Amaranthaceae family plants, Cactaceae family plants, Chenopodiaceae family plants, Cucurbitaceae family plants, Anacardiaceae family plants, Portulacaceae family plants, Urticaceae family plants, Lauraceae family plants, Liliaceae family plants, Iridaceae family plants, Orchidaceae family plants, Acanthaceae family plants, Caryophyllaceae family plants, corn plants, rice plants, wheat plants, sorghum plants, and canola plants. In some embodiments, the pollinating comprises manually applying or spraying the pollen onto a female reproductive part of the plant. Non-limiting examples of manual application include applying pollen with a cotton swab or small brush to the female reproductive part of a recipient plant, shaking or tapping a cryovial comprising pollen above the female reproductive part of a recipient plant to sprinkle the pollen onto the female reproductive part, and using a measuring spoon to transfer pollen from a container, such as a bag or graduated tube, to the female reproductive part of a recipient plant. Spraying may include but is not limited to air-assisted spraying or spraying using a common agricultural nozzle. In particular embodiments, pollinating may comprise applying electrostatically charged pollen to the female reproductive part of a recipient plant using any electrostatic pollen application technique known in the art. In one embodiment, pollinating comprises delivering pollen that is defined as free or substantially free of an added liquid, for example, water or another liquid. In another embodiment, pollinating comprising delivering pollen that is defined as dry or substantially dry. In yet another embodiment, the pollinating comprises delivering pollen that is mixed with a liquid prior to pollinating. In still yet another embodiment, the pollen may be delivered as a liquid pollen suspension solution.

In certain embodiments, the dried pollen is stored according to the methods described herein prior to pollinating the recipient plant. The pollen may be stored, for example, for up to about 1 year, 5 years, 10 years, 15 years, 20 years, 25 years, or 30 years prior to pollinating. The pollen may be stored in other embodiments for at least about 15 minutes, 1 hour, 12 hours, 1 day, 1 week, 1 month, 3 months, 6 months, or 1 year prior to the pollinating. The pollen may be stored at a temperature between about −196° C. and about −60° C. prior to the pollinating. The storage temperature may be, for example, about −196° C., −190° C., −180° C., −170° C., −160° C., −150° C., −140° C., −130° C., −120° C., −110° C., −100° C., −90° C., −80° C., −75° C., −70° C., −65° C., or −60° C. In one embodiment, the storage temperature is less than about −60° C.

In particular embodiments, the methods described herein produce at least about 1 seed, 5 seeds, 10 seeds, 15 seeds, 20 seeds, 25 seeds, 30 seeds, 35 seeds, 40 seeds, 45 seeds, 50 seeds, 55 seeds, 60 seeds, 65 seeds, 70 seeds, 75 seeds, 80 seeds, 85 seeds, 90 seeds, 95 seeds, or 100 seeds. In other embodiments, the methods described herein produce at least about 1 seed, 5 seeds, 10 seeds, 15 seeds, 20 seeds, 25 seeds, 30 seeds, 35 seeds, 40 seeds, 45 seeds, 50 seeds, 55 seeds, 60 seeds, 65 seeds, 70 seeds, 75 seeds, 80 seeds, 85 seeds, 90 seeds, 95 seeds, or 100 seeds per 5 mg of pollen used for the pollinating. In one embodiment, the pollinating produces a substantially equivalent number of seeds compared to the number of seeds produced from pollination under the same conditions but using pollen that was not dried. In another embodiment, the pollinating produces a substantially equivalent number of seeds compared to the number of seeds produced from pollination under the same conditions but using pollen that was not stored. Substantial equivalence is evaluated by comparing seed sets produced using pollen stored according to the methods provided herein to seed sets produced using pollen that was not dried and/or stored. As used herein, "substantially equivalent" refers to a characteristic wherein the mean value±standard deviation of the test population does not deviate more than about 20% from the mean value±standard deviation of the control population.

The step of collecting seed resulting from pollinating with pollen dried or stored according to the methods of the invention is provided herein. In a particular embodiment, a progeny plant produced from the collected seed may be crossed with itself or a different plant. In certain embodiments, a method of producing hybrid seed is provided herein comprising producing a pollen using the systems and methods described herein, delivering the pollen to a female reproductive part of a recipient plant, thereby pollinating the female reproductive part with the pollen from the donor plant, harvesting seed produced from the pollination; and identifying hybrid progeny. Selecting a progeny seed or plant that results from pollinating with pollen dried or stored may also performed. Identifying and selecting progeny could be facilitated by use of a polymorphic marker allele contained in the pollen donor that serves to identify progeny plants or seeds of that donor. Morphological markers or biochemical/protein markers have commonly been used as tools for selection of plants with desired traits in breeding. Molecular marker techniques that have been extensively used and are particularly promising for application to plant breeding include: restriction fragment length polymorphisms (RFLPs), amplified fragment length polymorphisms (AFLPs), random amplified polymorphic DNA (RAPD), microsatellites or simple sequence repeats (SSRs), and single nucleotide polymorphisms (SNPs) (Al-Khayri, et al., *Advances in Plant Breeding Strategies,* 2016).

In yet another embodiment, the method further comprises repeating the steps of (a) obtaining pollen according the methods of drying or storing pollen provided herein; and (b) pollinating the plant with the pollen, on two or more consecutive days. These steps may be repeated, for example, on two consecutive days, three consecutive days, four consecutive days, or on five or more consecutive days. In corn, for example, it can be found that repeating the delivering steps on two or three consecutive days can result in higher seed set.

In still other embodiments, the methods described herein may comprise pollination of flowers that are male sterile at the time of pollinating. Depending upon the developmental stage of the plant, donor pollen applied for cross-pollination could compete with pollen produced by the recipient plant. In order to improve the efficacy of the cross-pollination, it may be advantageous in some cases that the recipient plant be male sterile in an effort to reduce competition with selfing. Thus, a male sterility system could be employed with the female parent plant in a particular cross. Many such male sterility systems are well known, including cytoplasmic male sterility (CMS) and genic male sterility (GMS). CMS and GMS facilitate hybrid seed production for many crops and thus allow breeders to harness yield gains associated with hybrid vigor. The use of a gametocide presents an alternative method to produce male sterility. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of Roundup herbicide in combination with glyphosate tolerant corn plants to produce male sterile corn plants is disclosed in PCT Publication WO 98/44140. Several gametocides have been reported effective in inducing pollen sterility in various crops and are well known in the art. Such gametocides include sodium methyl arsenate, 2,3-dichloroisobutyrate, sodium 2,2-dichloropropionate, gibberellic acid, maleic hydrazide (1,2-dihydropyridazine-3,6-dione), 2,4-dichlorophenoxyacetic acid, ethyl 4-fluorooxanilate, trihalogenated methylsulfonamides, ethyl and methyl arsenates (Ali et al., *Genetics Plant Breeding,* 59:429-436, 1999). Physical emasculation of the recipient plant presents another alternative to produce male sterility. Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because the male reproductive portion, and thereby pollen bearing parts, have been previously removed from all plants of the plant being used as the female in the hybridization. Of course, during this hybridization procedure, the parental varieties are grown such that they are isolated from other plants to minimize or prevent any accidental contamination of pollen from foreign sources. These isolation techniques are well within the ability of those skilled in this art.

The methods disclosed herein may be implemented for improved cross-pollination of potentially any plants. Such plants can include, but are not limited to, cereal plants, non-limiting examples of which are corn, wheat, rice, and sorghum.

Modified Plants and Seeds

One aspect of the invention provides selection of progeny plants and seeds that result from the methods described herein. In some embodiments, the progeny plants and seeds may be defined as comprising a detectable modification relative to the female parent plant. One method of producing such plants and seeds is through use of an allele produced by plant genetic transformation. Suitable methods for transformation of host plant cells for use with the current invention are well known in the art and include any method by which DNA can be introduced into a cell (for example, where a recombinant DNA construct is stably integrated into a plant chromosome) and are well known in the art. Some widely utilized methods for cell transformation are *Agrobacterium*-mediated transformation, microprojectile bombardment-mediated transformation, and cell penetrating peptide-mediated delivery of DNA modifying agents.

Another method of producing modified plants and seeds is through genome editing. As used herein, the term "genome editing" refers to the use of genome editing methods and a site-specific genome modification enzyme to modify a nucleotide sequence. In some embodiments, donor pollen may be transformed using techniques known in the art to contain one or more reagents that mediate genome-specific modification in a plant. In other embodiments, donor pollen may be collected from a transgenic plant transformed using techniques known in the art. Pollen grains may be used in accordance with the invention that comprise any such reagents of loci generated with use of such reagents at any current or prior generation.

Suitable methods for altering a wild-type DNA sequence at a pre-determined chromosomal site include any method known in the art. Targeted modification of plant genomes through the use of genome editing methods and reagents can be used to create improved plant lines through modification of plant genomic DNA. In addition, genome editing methods and reagents can facilitate targeted insertion of one or more nucleic acids of interest into a plant genome. Exemplary methods for introducing donor polynucleotides into a plant genome or modifying the genomic DNA of a plant include the use of genome editing reagents such as: sequence-specific recombinases, endonucleases, zinc-finger nucleases, engineered or native meganucleases, TALE-endonucleases, RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system), and CRISPR-associated transposases (Strecker, et al., *Science,* 365(6448):48-53, 2019) and (Klompe, et al., *Nature,* 571: 219-225, 2019). Several embodiments relate to methods of genome editing using single-stranded oligonucleotides to introduce precise base pair modifications in a plant genome, as described by Sauer et al. (*Plant Physiol.* 170(4):1917-1928; 2016).

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

EXAMPLES

Example 1. Analysis of Seed Set Using Stored Corn Pollen

Achieving seed set using stored pollen is challenging. Pollen viability can be lost in minutes to hours after shed depending on the species and environmental conditions. Pollen storage systems and methods were developed to overcome these challenges. The effects of pollen storage was evaluated by examining seed set following pollination according to the following protocol. Approximately 4.0 grams of corn pollen was open-collected, passed through a 600 μm sieve to remove anthers and other larger debris, and placed in a polyethylene weigh boat in a container above a $KNO_3$ slurry (Greenspan, *J Res NBS Phys Chem*, 81A:89-96, 1977). Pollen was stored in the $KNO_3$ chamber for approximately 1 hour at 4° C. and 96% humidity. Following storage the pollen was passed through a 180 μm sieve to remove large clumps and to ensure particle size homogeneity. Samples were taken to evaluate pollen germination and measure initial moisture content using a halogen moisture balance. The remaining pollen was divided into two 1.5 g aliquots for drying. The germination scores of the pollen prior to and after drying were 84% and 73%, respectively.

Pollen was dried using a fluidized bed dryer comprising multiple mass flow controllers (Alicat Scientific®), flexible vinyl tubing, multiple 0.75" ID polycarbonate columns comprising filters at both the inlet and the outlet, multiple relative humidity and temperature probes (Rotronics®), multiple vibratory bases, and a personal computer programmed to calculate the moisture content of the pollen samples at any time based on the starting moisture content, the relative humidity of the drier exhaust, and the mass flow of dry air. A schematic representing each individual drying system is illustrated in FIG. 7. Pollen aliquots were transferred into individual drying systems and dried with dry air at a flow rate of 4.5 standard cubic feet per hour (SCFH). Drying was stopped when the computer program indicated that the wet basis moisture content was about 25%. The wet basis moisture content measurements of the pollen before and after drying were 55.5% and 24.3%, respectively.

Dried pollen was divided into 0.15 mL aliquots and placed into 2.0 mL polypropylene cryovials. The cryovials were capped, transferred to a plastic rack, and immersed in liquid nitrogen to rapidly freeze. Samples were stored submersed in liquid nitrogen for 1 hour prior to performing pollinations.

Following storage, each cryovial was warmed under ambient greenhouse conditions (28° C., 40% RH). Pollen was prepared for pollination by allowing the cryovial to equilibrate at ambient greenhouse conditions for 10 seconds; tapping the vial to mix pollen; opening the cryovial 20 seconds after removing from liquid nitrogen; and pouring the pollen from the cryovial onto the silk of a recipient plant 30 seconds after removing from liquid nitrogen. Seed set was examined 14 days post pollination. Pollination with stored pollen was able to set seed as shown in FIG. 11.

Figure 12:
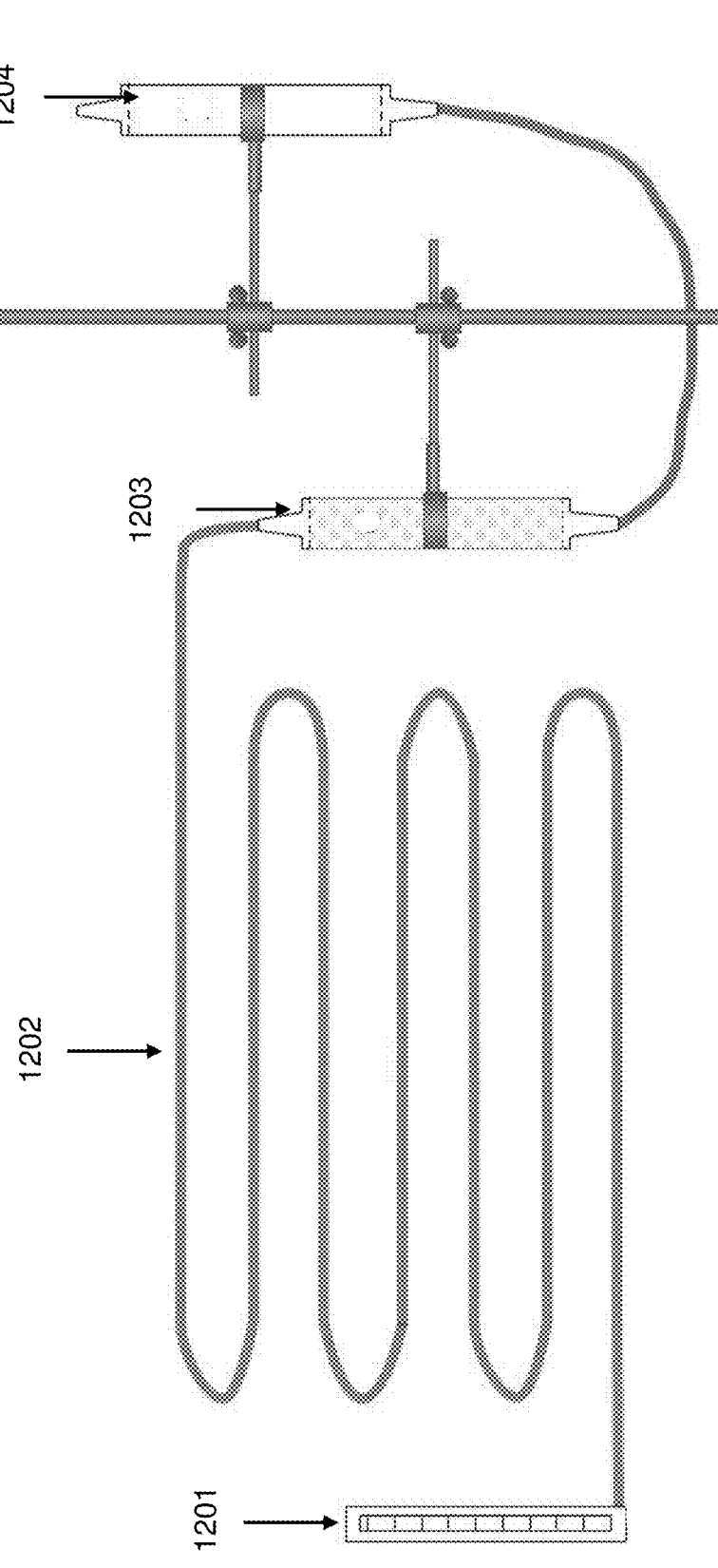
FIG. 12 shows a diagram of one embodiment of the current disclosure comprising a drying apparatus.

Example 2. Analysis of Pollen Drying Parameters Using Differential Scanning Calorimetry Existing methods for drying and/or storing recalcitrant or monocot pollen do not provide reproducible results, as numerous studies have demonstrated that excessive drying leads to irreversible desiccation damage. The present invention provides a significant advancement over the prior art by providing systems and methods that measure or predict pollen moisture content in real-time during drying. Precise drying requirements are essential to successful cryopreservation of recalcitrant or monocot pollen, non-limiting examples of which include corn, rice, wheat, sorghum, and canola pollen. Reproducible, successful cryopreservation requires that enough moisture be removed to minimize the risk of ice formation during cooling, but also that enough moisture be retained such that the pollen is not irreversibly damaged prior to freezing. The moisture content of the sample prior to freezing, the freezing rate, and the thawing rate are important parameters to consider in order to achieve reproducible results. Differential scanning calorimetry (DSC) was used as an analytical tool to evaluate the role of these parameters according to the following protocol. A fluidized bed dryer was constructed comprising a pressure regulator, flexible vinyl tubing, a 3 meter ⅜" copper coil, a Drierite® column (Drierite®, Product #26930), a gas rotameter (Brooks Instruments™, Model #MR3A04SVVT) and an empty Drierite® column. FIG. 12 is a diagram of the drying apparatus comprising a gas rotameter 1201, a copper coil heat exchanger 1202, a desiccant dryer 1203, and an empty column 1204. The entire fluidized bed dryer was placed in a growth chamber maintained at about 4° C. and about 40% relative humidity.

Pollen was transferred to the empty Drierite® column, fluidized with nitrogen gas maintained at approximately 10 psi with an airflow rate of 3 to 4 SCFH. The surface of the bed was well defined and bubbling and channeling was visible under these conditions. Samples were taken at 0, 10, 20, 35, 50, and 70 minutes of cumulative drying. The samples were further divided into aliquots for germination scoring, moisture content analysis, and differential scanning calorimetry.

The pollen moisture content of the samples was determined using a loss-on-weight measurement. The samples were weighed, placed in a benchtop convective oven at 105° C. for 16 hours, and weighed again upon removal from the oven. The pollen moisture content (PMC) was calculated on both wet and dry basis as described in Equation 1 and Equation 2.

$$PMC(\% \ w.b.) = \frac{\text{Fresh Weight} - \text{Dry Weight}}{\text{Fresh Weight}} * 100\% \qquad (1)$$

$$PMC(\% \ d.b.) = \frac{\text{Fresh Weight} - \text{Dry Weight}}{\text{Dry Weight}} * 100\% \qquad (2)$$

Germination was evaluated by dusting pollen samples onto plates of solid germination media and incubating at room temperature for 4 hours. A single plate was prepared for each time sample. Following incubation, plates were stored at 4° C. for 1 day prior to grading. Germination scores were determined by counting the percentage of grains that developed tubes with a length of at least twice the grain diameter. For each plate, a minimum of 300 grains were included in the measurement.

Differential scanning calorimetry was performed using Mettler Toledo DSC1 and 40 μL aluminum crucibles to obtain heating and cooling thermograms of each time sample. The DSC1 was programmed to first cool the sample from 25° C. to −80° C. at a constant rate of −10° C./min, hold the sample at −80° C. for 10 minutes, and then reheat the sample to 25° C. at a rate of 10° C./min.

Mettler Toledo STARe software was used to baseline correct the data and to integrate ice formation and melting peaks. The transition enthalpy per gram of dry weight was calculated from the peak areas of the cooling and heating thermograms using Equation 3.

$$\Delta H_{transition} = \frac{\text{Peak Area } [W \cdot {}^{\circ}\text{C.}]}{\text{Heating Rate } \left[\frac{{}^{\circ}\text{C.}}{s}\right] \cdot \text{Dry Weight } [g]} \quad (3)$$

Figure 13:
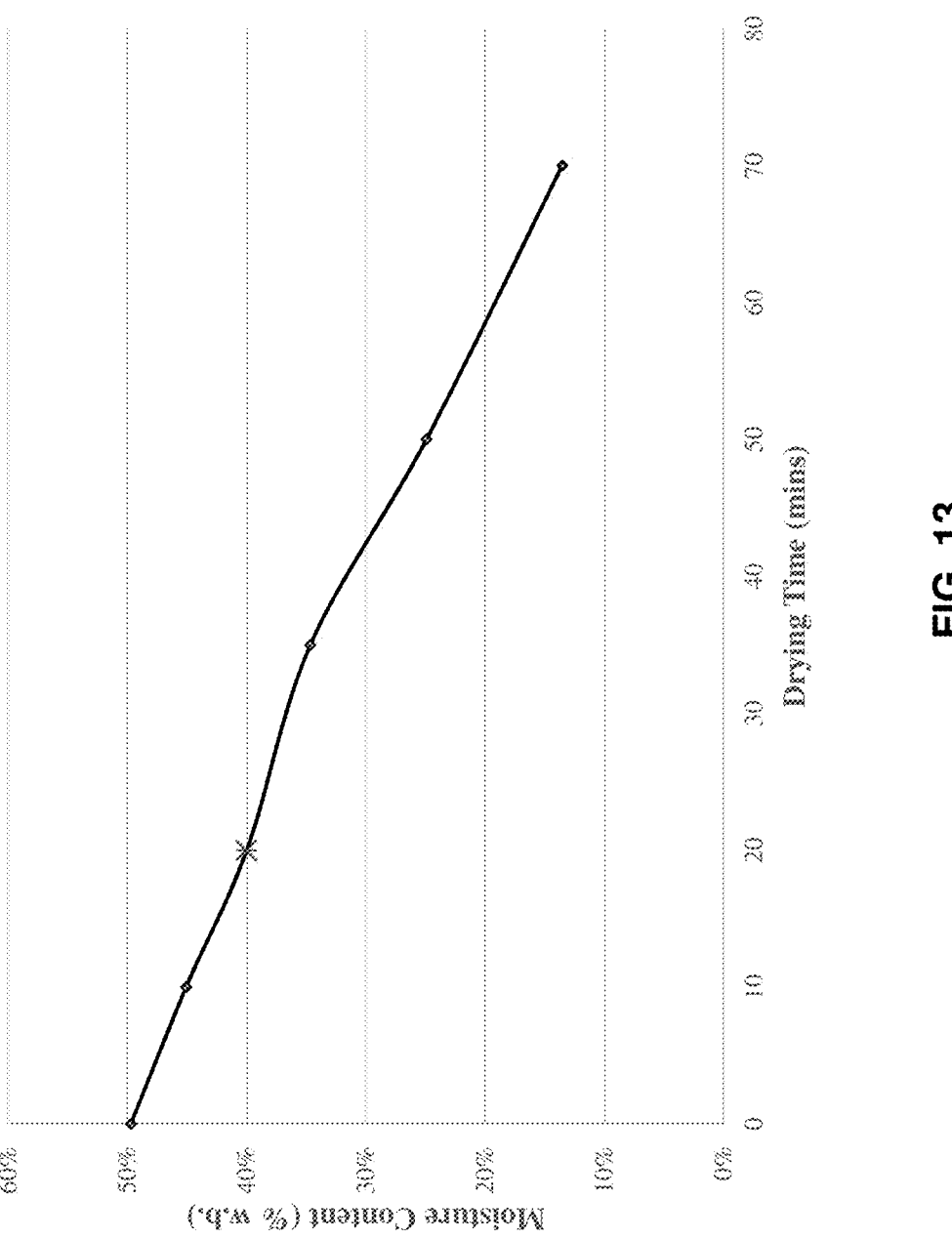
FIG. 13 shows a representative plot of the wet-basis moisture content versus drying time obtained using the drying apparatus of FIG. 12.

A plot of the wet-basis moisture content versus drying time is shown in FIG. 13. In contrast to drying curves obtained at higher temperatures, which have distinct constant rate and falling rate regions, the drying curve at 4° C. exhibits linear behavior. This suggests that heat transfer is likely the rate limiting phenomena at lower drying temperatures.

Figure 14:
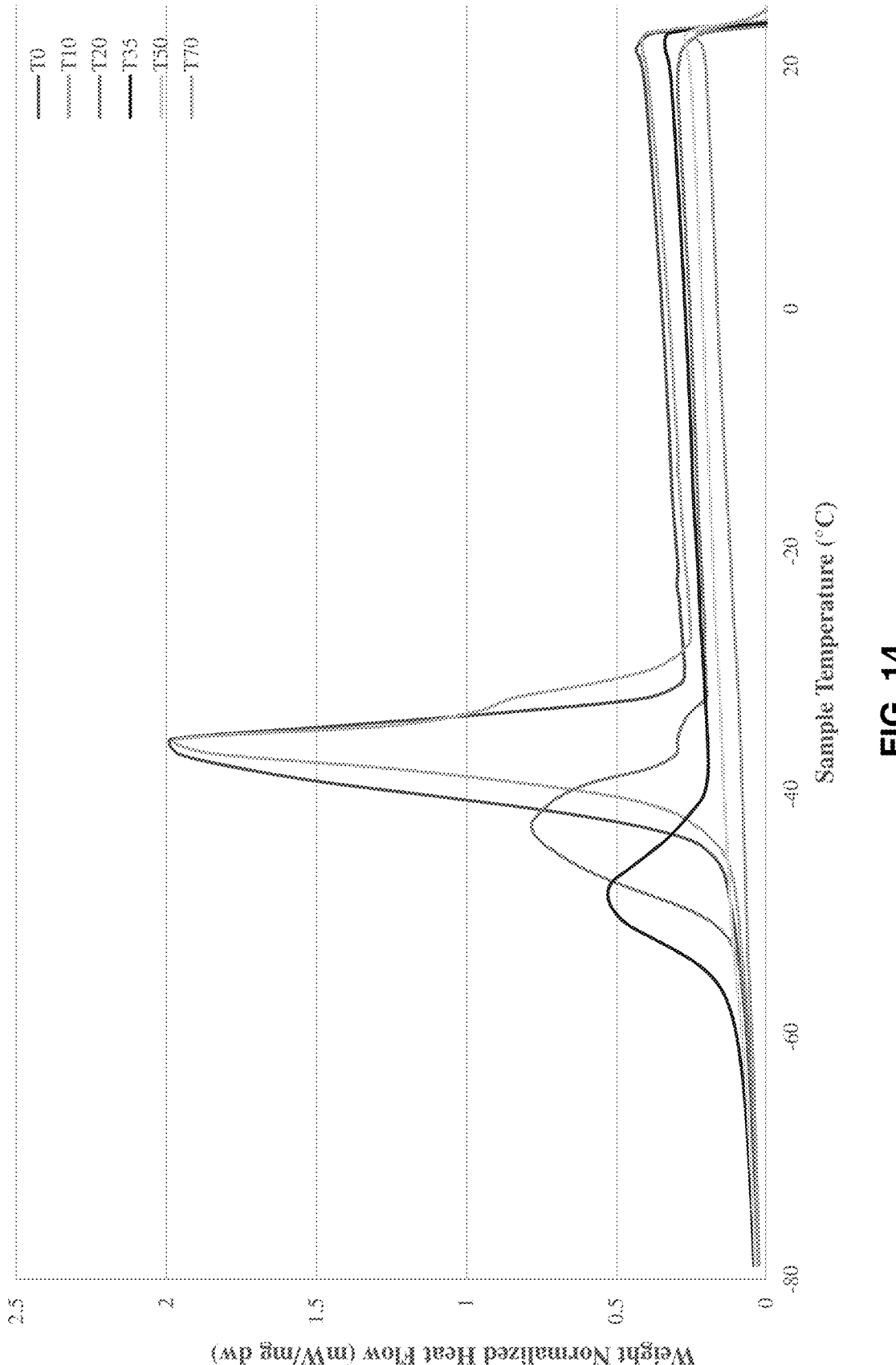
FIG. 14 shows a representative plot of dry weight normalized cooling thermograms obtained using the drying apparatus of FIG. 12.
Figure 15:
FIG. 15 shows a representative plot of dry weight normalized heating thermograms obtained using the drying apparatus of FIG. 12.

Heating and cooling thermograms are shown in FIG. 14 and FIG. 15. In both the heating and cooling thermograms, prominent peaks associated with the formation and melting of ice crystals in the samples are clearly present. Peaks are produced in the thermograms when water within the sample transitions between phases, such as from a solid phase to a liquid phase or from a liquid phase to a solid phase, which results in a sudden change in latent heat flow. The wet basis moisture contents of the samples labeled T0, T10, T20, T35, T50, and T70 are 50%, 45%, 40%, 35%, 25%, and 14%, respectively. As shown in FIG. 14, the area under the peak increases as the water content of the sample increases, which represents increased ice crystal formation and mechanical stress. Importantly, the cooling thermograms of sample T50 and T70, which have a wet basis moisture content of 25% and 14%, respectively, do not comprise a peak, indicating that the liquid water in these samples does not transition to a solid phase. The absence of a peak in these samples indicates that when the wet basis moisture content of pollen is low enough, ice crystal formation and mechanical stress can be avoided during cooling. As shown in FIG. 14, the onset of ice formation in samples with higher wet basis moisture contents, for example 50%, 45%, 40%, or 35%, occurs over a temperature range between about −25° C. and about −40° C. This is much lower than the temperature range of ice formation for pure water and dilute solutions. The peak areas of the cooling thermograms are lower than the peak areas in the heating thermograms for the higher moisture content samples, suggesting that additional ice formation occurred during the isothermal hold. These observations suggest that the extent of ice formation may be controlled in part by the rate of cooling. The baseline shift at approximately −75° C. in the heating thermograms (FIG. 15) of the low moisture content samples may be indicative of devitrification from a glass phase, but no peaks are present that are indicative of the melting of ice crystals in these samples. In some embodiments, it may be desired to store pollen at a temperature which is below the glass transition temperature.

Figure 16:
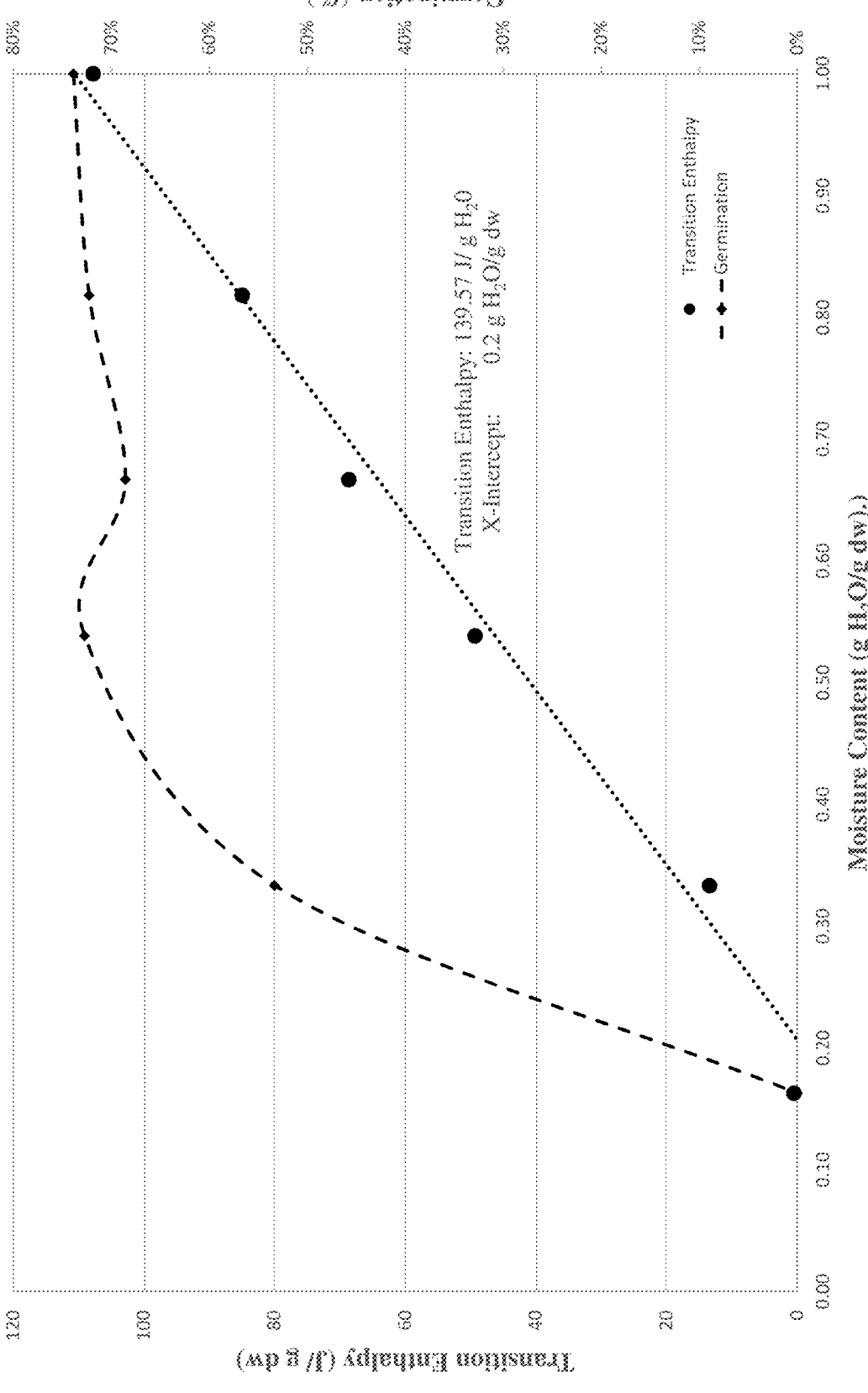
FIG. 16 shows a representative plot of the transition enthalpy per dry weight versus moisture content obtained using the drying apparatus of FIG. 12 with germination rate superimposed.

The transition enthalpy per gram of dry weight was calculated from the heating thermograms using methods known in the art (Buitink, et al., *Plant Physiol.*, 111:235-242, 1996). The transition enthalpy per gram dry weight was plotted against the dry-basis moisture content and the germination score (FIG. 16), and a linear regression was performed using the non-zero enthalpy values. The slope of the regression line represents the transition enthalpy of water in the sample and the x-intercept represents the moisture content below which any remaining water does not freeze. The calculated transition enthalpy is 139 j/g $H_2O$. FIG. 16 further demonstrates that the germination remains relatively constant before rapidly declining when the dry basis moisture content is less than 0.4. The point at which germination becomes zero corresponds with the x-intercept of the transition enthalpy regression line, suggesting that removal of the "non-freezing" water is detrimental to the pollen. Therefore, the systems and methods described herein may be used to precisely dry pollen to a desired moisture content, which may in some embodiments be a moisture content higher than the moisture content at which removal of "non-freezing" water begins. Drying to such a desired moisture content may be desired to prevent ice crystal formation and decrease mechanical stress, thus preserving viability and fertility following storage. In addition, the kinetics of ice formation may be surpassed to reach a temperature where the glass phase is thermodynamically favorable when higher rates of freezing are used, for example, a rate of freezing greater than about 200° C./min (Nath and Anderson, *Cryobiology*, 12(1): 81-8, 1975). Similarly, rapid rates of thawing may allow the sample to reach the melting temperature before appreciable ice formation occurs.

Example 3. Real-Time Approximation of Pollen Moisture Content

A real-time approximation of the pollen moisture content may be determined using the systems and methods of the present invention. In one embodiment, the initial mass of water and the total dry mass may be calculated from the initial moisture content and sample weight of the pollen according to Equation 4 and Equation 5:

$$m_{H2O,initial} = \frac{PMC_{initial}}{100} \cdot m_{total,initial} \quad (4)$$

$$\text{dry mass} = \left(\frac{(100 - PMC_{initial})}{100}\right) \cdot m_{total,initial} \quad (5)$$

In another embodiment, the mass of water in the pollen sample at any time may be calculated according to Equation 6:

$$m_{H2O}(t) = m_{H2O,initial} - \int_0^t \dot{m}_{H2O,exhaust} dt \quad (6)$$

In yet another embodiment, the mass flow rate of water in the drier exhaust in Equation 6 may be calculated using the temperature, relative humidity, pressure, and mass flow rate of the drier exhaust gas as described below. The integral in Equation 6 may be approximated for example by taking the sum of the total mass of water lost over 1 second intervals.

Relative humidity is defined as the ratio of the actual water vapor pressure, $P_w(T)$, to the saturated vapor pressure, $P_{ws}(T)$, at a given temperature as shown in Equation 7 and may be expressed as a percentage.

$$RH = \frac{P_w(T)}{P_{ws}(T)} \cdot 100\% \quad (7)$$

In still yet another embodiment, the saturated vapor pressure of water in hPa may be accurately approximated over the temperature range of −20° C. to +50° C. using Equation 8.

$$P_{ws} = 6.116441 hPa \cdot 10^{\left(\frac{7.591386 \cdot T}{T+240.7263}\right)} \quad (8)$$

In one embodiment, the water vapor pressure in the drier exhaust may be calculated by combining Equation 7 and Equation 8 and substituting the relative humidity and temperature measurements from the instrument as shown in Equation 9.

$$P_w(T) = \left(\frac{RH(\%)}{100\%}\right) \cdot 6.116441 hPa \cdot 10^{\left(\frac{7.591386 \cdot T}{T+240.7263}\right)} \quad (9)$$

In another embodiment, it may be assumed that the drying exhaust is a two-component system, comprising a drying gas and water vapor. Although air is a mixture of gases it may be treated for example as a single gas using an average molecular weight. The total pressure of the system for example may be calculated according to Equation 10.

$$P_w + P_{gas} = P_{total} \quad (10)$$

In yet another embodiment, it may be assumed that gas behaves ideally and the ratio of the moles of water vapor to the moles of drying gas may be expressed as a ratio of their partial pressures as shown in Equation 11.

$$\frac{n_w}{n_{gas}} = \frac{P_w}{P_{total} - P_w} \quad (11)$$

In still yet another embodiment, the mixing ratio of a gas (X) is defined as the mass of water vapor per mass of dry gas. The mass of water vapor and gas may be expressed as shown in Equation 12.

$$X = \frac{m_w}{m_{gas}} = \frac{n_w MW_w}{n_{gas} MW_{gas}} \quad (12)$$

In one embodiment, Equation 11 may be substituted into Equation 12 to calculate the mixing ratio of the gas (X) as shown in Equation 13, where $MW_w$=18.02 g/mol and $MW_{gas}$=28.97 g/mol (for air).

$$X = \left(\frac{P_w}{P_{total} - P_w}\right)\left(\frac{MW_w}{MW_{gas}}\right) \quad (13)$$

In another embodiment, the mass flow rate of water in the drier exhaust, $\dot{m}_w$, is approximately equal to the product of the mass flow rate of the drying gas and the mixing ratio as shown in Equation 14.

$$\dot{m}_w = \dot{m}_{gas} X \quad (14)$$

Equation 9 may for example be substituted into Equation 13 and the resulting combination substituted into Equation 14 to yield an expression for the mass flow rate of water in the drier exhaust as a function of the relative humidity, temperature, pressure, and mass flow rate. This expression may be for example substituted into Equation 6 to solve for the amount of water lost during drying.

In another embodiment, the wet-basis pollen moisture content may be calculated at any time using Equation 15.

$$PMC(t) = \frac{m_{H2O}(t)}{m_{H2O}(t) + \text{dry mass}} \quad (15)$$

Example 4. Methods for Thawing Cryopreserved Pollen

Existing methods for drying, storing, and/or thawing recalcitrant or monocot pollen do not provide reproducible results. Precise drying requirements are essential to successful cryopreservation of recalcitrant or monocot pollen, non-limiting examples of which include corn, rice, wheat, and sorghum pollen. Reproducible, successful cryopreservation requires that enough moisture be removed to minimize the risk of ice formation during cooling, but also that enough moisture be retained such that the pollen is not irreversibly damaged prior to freezing. The moisture content of the sample prior to freezing, the freezing rate, and the thawing rate are important parameters to consider in order to achieve reproducible results. Pollen cytoplasm is vitrified to reach a glass phase state during freezing, which minimizes ice crystal formation and mechanical stress. Therefore to preserve maximum pollen viability during the thawing stage, pollen must be warmed at a rate that prevents ice crystal formation and mechanical stress. The critical warming rate correlates with the moisture content of the pollen and can be determined empirically using the methods described herein. It may be desired for example to warm pollen as rapidly as possible as the temperature approaches and traverses the glass transition temperature and at temperatures higher than the glass transition temperature, however, it may be desired to warm pollen at a slower rate when the temperature of the pollen is substantially below the glass transition temperature. The glass transition temperature may vary for each pollen intracellular component, thus warming as rapidly as possible as the temperature approaches and traverses this temperature prevents ice formation and decreases mechanical stress. Pollen may be warmed for example by removing a cryovial of cryopreserved pollen from liquid nitrogen and immediately pouring the pollen from the cryovial onto the stigma of a recipient plant at ambient greenhouse temperatures. Any method known in the art which is capable of warming at a similar rate may be used. The pollen may for example be warmed at a rate of at least about 10° C./min. The warming rate may be for example at least about 10° C./min, 20° C./min, 40° C./min, 60° C./min, 80° C./min, 100° C./min, 200° C./min, 300° C./min, 400° C./min, 500° C./min, 600° C./min, 700° C./min, 800° C./min, 900° C./min, 1000° C./min, 1500° C./min, 2000° C./min, 2500°

C./min, 3000° C./min, 3500° C./min, 4000° C./min, 4500° C./min, or 5000° C./min, including all ranges derivable therebetween.

In one aspect, the present disclosure provides a rapid thawing procedure comprising: a) obtaining a pollen sample stored at a storage temperature less than about –60° C., for example the sample may have been stored at about –60° C., –70° C., –80° C., –140° C., or –196° C.; b) thawing the sample at ambient temperature. In one embodiment, the pollen is directly applied to a recipient plant following the thawing. In another embodiment, the pollen sample is transferred from long-term storage to a transportable dewar. In yet another embodiment, the dewar comprises liquid nitrogen or dry ice. In still yet another embodiment, the dewar is transported to the recipient plant. The recipient plant may be, for example, in a greenhouse or field area. In still yet another embodiment, the pollen sample is placed at ambient temperature to thaw. In one embodiment, the container, one example of which is a cryovial, is agitated in a manner such that the pollen in the container is collected in the bottom of the container. In another embodiment, the pollen is applied to the recipient plant about 20 seconds, 30 seconds, 40 seconds, 1 min, 2 min, or 5 min after being placed at ambient temperature.

As an illustrative example, seed set was evaluated following a direct apply thawing method as described below. A cryovial containing pollen with a wet basis moisture content of about 25% was removed from storage at –196° C., transferred to a dewar containing liquid nitrogen, and transported to a greenhouse containing female plants. The cryovial was removed from the dewar and placed at ambient temperature. The bottom of the cryovial was tapped 3-4 times to collect pollen at the bottom approximately 10 seconds after the cryovial was removed from the dewar, the cap of the cryovial was removed approximately 20 seconds after the cryovial was removed from the cryovial, and the pollen was poured onto the silks of a recipient female plant approximately 30 seconds after the cryovial was removed from the dewar. Seed set produced using the direct apply thawing method is shown in Table 1.

TABLE 1

| Seed set produced using a direct apply method. | | | |
|---|---|---|---|
| Pollen | Ear 1 | Ear 2 | Ear 3 |
| Fresh pollen | 344 | NA | NA |
| Cryopreserved pollen with direct apply | 269 | 303 | 312 |

In another aspect, the present disclosure provides a rapid thawing procedure comprising: a) obtaining a pollen sample stored at a storage temperature less than about –60° C., for example the sample may have been stored at –60° C., –70° C., –80° C., –140° C., or –196° C.; b) thawing the sample at about 37° C. In one embodiment, the pollen is directly applied to a recipient plant following the thawing. In another embodiment, the pollen sample is transferred from long-term storage to a transportable dewar. In yet another embodiment, the dewar comprises liquid nitrogen or dry ice. In still yet another embodiment, the dewar is transported to the recipient plant. The recipient plant may be, for example, in a greenhouse or field area. In still yet another embodiment, the pollen sample is placed in a 37° C. water bath. In one embodiment, the pollen sample may be allowed to thaw for about 20 seconds, 30 seconds, 40 seconds, 1 min, 2 min, or 5 min at 37° C. prior to being applied to a recipient plant. In another embodiment, the container may be swirled during the 37° C. incubation period. In another embodiment, the container, one example of which is a cryovial, is agitated in a manner such that the pollen in the container is collected in the bottom of the container. In another embodiment, the pollen is allowed to thaw at ambient temperature for about 20 seconds, 30 seconds, 40 seconds, 1 min, 2 min, or 5 min after prior to being transferred to 37° C.

As an illustrative example, seed set was evaluated using a water bath thawing method as described below. A cryovial containing pollen with a wet basis moisture content of about 25% was removed from storage at –196° C., transferred to a dewar containing liquid nitrogen, and transported to a greenhouse containing female plants. The cryovial was removed from the dewar and placed at ambient temperature. The bottom of the cryovial was tapped 3-4 times to collect pollen at the bottom approximately 10 seconds after the cryovial was removed from the dewar, the cryovial was placed in a 37° C. water bath approximately 30 seconds after the cryovial was removed from the dewar and then swirled for approximately 1 minute. Next the pollen was transferred from the cryovial into a plastic weight boat and poured directly onto the silks of a female recipient plant. Seed set produced using the water bath thawing method is shown in Table 2.

TABLE 2

| Seed set produced using a water bath method. | | | |
|---|---|---|---|
| Pollen | Ear 1 | Ear 2 | Ear 3 |
| Fresh pollen | 352 | NA | NA |
| Cryopreserved pollen with water thaw | 117 | 170 | 142 |

In yet another aspect, the present disclosure provides a rapid thawing procedure comprising: a) obtaining a pollen sample stored at a storage temperature less than about –60° C., for example the sample may have been stored at –60° C., –70° C., –80° C., –140° C., or –196° C.; b) applying a gas with a temperature between about 30° C. and about 50° C. to the sample. In one embodiment, the gas is air. In another embodiment, the temperature of the gas is about 20° C., 25° C., 30° C., 35° C., 40° C., 45° C., or 50° C., including all ranges derivable therebetween. In yet another embodiment, the pollen is directly applied to a recipient plant following the thawing. In still yet another embodiment, the gas is applied to the sample for about 5 seconds, 10 seconds, 20 seconds, 30 seconds, 45 seconds, or 1 minute prior to being applied to the recipient plant. In one embodiment, the pollen sample is transferred from long-term storage to a transportable dewar. In another embodiment, the dewar comprises liquid nitrogen or dry ice. In yet another embodiment, the dewar is transported to the recipient plant. The recipient plant may be, for example, in a greenhouse or field area. In still yet another embodiment, the pollen sample is transferred from the container to a tray prior to applying the gas. In one embodiment, the tray is covered with a filter prior the applying the gas. The filter may have a pore size, for example, of less than about 150 μm, 120 μm, 100 μm, 80 μm, 60 μm, or 40 μm, including all ranges derivable therebetween. In another embodiment, the pollen is allowed to thaw at ambient temperature for about 20 seconds, 30 seconds, 40 seconds, 1 min, 2 min, or 5 min after prior to applying the gas. In yet another embodiment, the container, one example of which is a cryovial, is agitated in a manner such that the pollen in the container is collected in the bottom of the container.

As an illustrative example, seed set was evaluated using a warm air thawing method as described below. A cryovial containing pollen with a wet basis moisture content of about 25% was removed from storage at −196° C., transferred to a dewar containing liquid nitrogen, and transported to a greenhouse containing female plants. The cryovial was removed from the dewar and placed at ambient temperature. The bottom of the cryovial was tapped 3-4 times to collect pollen at the bottom approximately 10 seconds after the cryovial was removed from the dewar and was poured into a dish and covered with a 45 μm filter approximately 30 seconds after the cryovial was removed from the dewar. A heat gun was then used to blow air with a temperature of about 30° C. to about 50° C. onto the filter for 10-20 seconds. The pollen was then transferred to a plastic weight boat and poured directly onto the silks of a female recipient plant. Seed set produced using the warm air thawing method is shown in Table 3.

TABLE 3

| Seed set produced using a warm air thawing method. | | | |
|---|---|---|---|
| Pollen | Ear 1 | Ear 2 | Ear 3 |
| Fresh pollen | 385 | NA | NA |
| Cryopreserved pollen with Air thaw | 314 | 339 | 389 |

In still yet another aspect, the present disclosure provides a method for rehydrating pollen. In one embodiment, the method comprises thawing pollen using the methods provided herein prior to rehydrating the pollen. In another embodiment, the method comprises rehydrating the pollen using a temperature and humidity controlled air generator. In yet another embodiment, the temperature of the air may be about 20° C., 25° C., 30° C., or 35° C., including all ranges derivable therebetween. In still yet another embodiment, the sample may be rehydrated for about 20 minutes, 30 minutes, 1 hour, 2 hours, 3 hours, 4 hour, or 5 hours. In one embodiment, the pollen may be rehydrated in a column connected to a humidity controlled air generator. In another embodiment, the wet basis moisture content of the pollen following rehydration is between about 25% and about 50%. The wet basis moisture content of the pollen following rehydration may be for example about 25%, 30%, 35%, 40%, 45%, 50%, or 55%, including all ranges derivable therebetween.

Example 5. Liquid Phase Pollen Dehydration

In one embodiment, pollen may be dried to a desired moisture content using a hypertonic solution of a pollen impermeable solute. As used herein the term "impermeable" refers to a state where an isotonic solution of the solute when first mixed with pollen produces less than about 10% pollen lysis over the first 4 hours that the pollen is in contact with the solution. As used herein the term "hypertonic" refers to a state wherein the osmolarity of the extracellular solution is greater than the osmolarity of the pollen cytoplasmic space, resulting in efflux of water from the pollen. Virtually any impermeable solute may be used. Non-limiting examples of solutes that may be used in the production of such a liquid phase pollen dehydration solution include a monosaccharide solute, a disaccharide solute, a polysaccharide solute, a polyhydric alcohol solute, a polyethylene glycol solute, glucose, fructose, galactose, sucrose, lactose, maltose rehalose, cellobiose, chitobiose, kojibiose, nigerose, isomaltose, trehalose, sophorose, laminaribiose, gentiobiose, trehalulose, turanose, maltulose, leucrose, isomaltulose, gentiobiulose, mannobiose, melibiose, melibiulose, rutinose, rutinulose, xylobiose, maltotriose, melezitose, nigerotriose, maltotriulose, raffinose, kestose, maltodextrin, starch, glycogen, galactogen, cellulose, chitin, pectin, peptidoglycan, mannitol, sorbitol, xylitol, lactitol, isomalt, maltitol, sodium chloride, or polyethylene glycol. In one embodiment, the pollen is separated from the liquid phase pollen dehydration solution when a desired moisture content has been reached. The pollen may be separated from the liquid phase dehydration solution using any appropriate method of separating known in the art, non-limiting examples of which include centrifugation and filtration. Following separation the pollen may be cryopreserved using the methods described herein.

Example 6. Analysis of Pollen Germination on the Stigma

Figure 17:
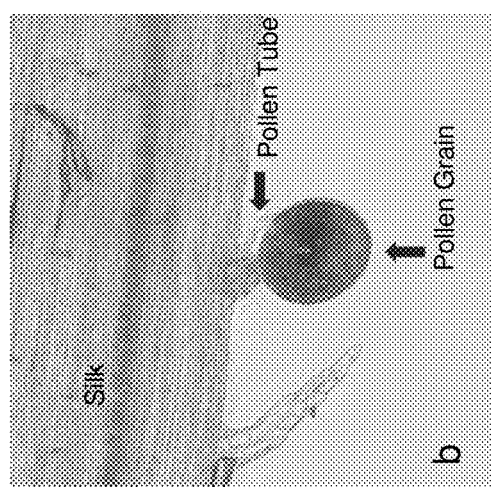
FIG. 17 shows (a-b) microscopic images of corn pollen adhered to corn silks; (c) quantitative data relating to the number of pollen grains adhered per cm silk; and (d) data demonstrating that the percentage of live pollen in a sample directly correlates with the number of pollen grains adhered per cm silk.
Figure 17:
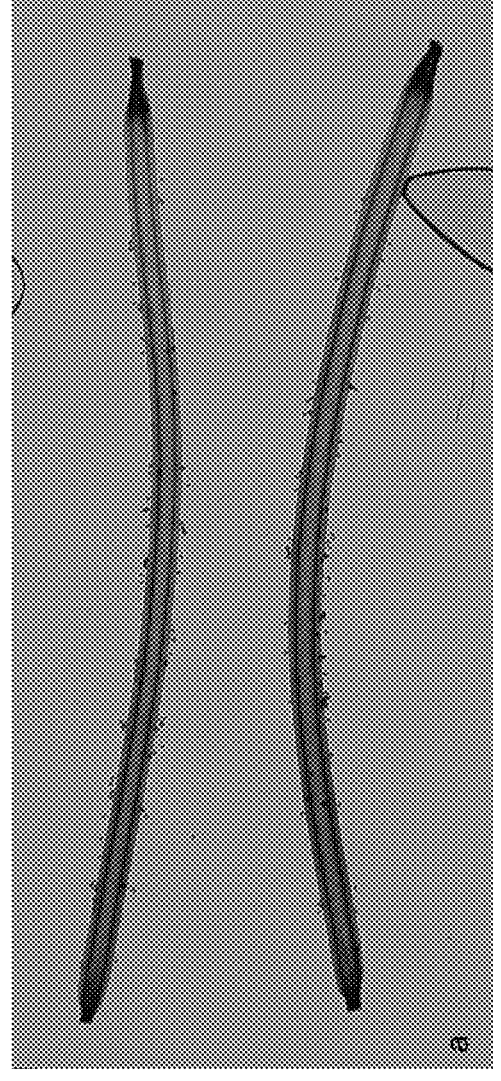
Figure 17:
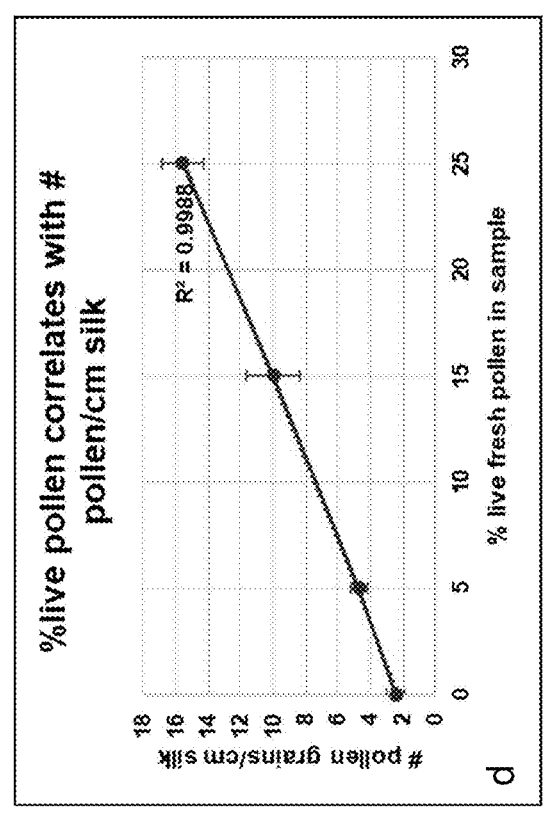
Figure 17:
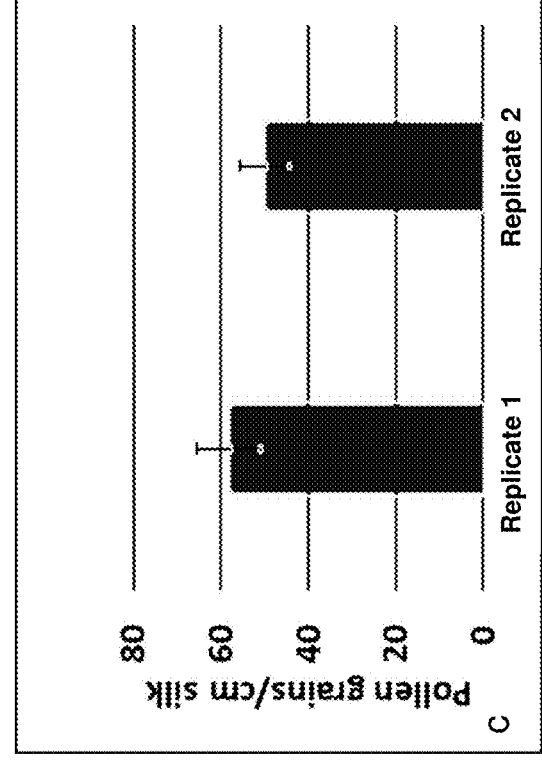

Assays to evaluate germination on the stigma are valuable tools used to determine pollen viability and fertility. Qualitative assays to evaluate germination on the stigma are known in the art. As one example, pollen may be applied to the stigma, incubated, fixed, stained using aniline blue, and visualized using UV dark field (Sari Gorla, et al., *Theoretical and Applied Genetics.* 46:289-294; 1975). Germination on the stigma may also be quantitative. For example, pollen may be applied to the stigma, incubated for 1-5 hours, washed, fixed, and visualized using microscopy. In specific embodiments, a brightfield microscope or a stereoscope may be used. Since pollen that has not formed a pollen tube is substantially removed during the wash step, this assay primarily identifies pollen which has formed a pollen tube and is adhered to the stigma. Microscopic images can be obtained and analyzed to determine the number of pollen grains adhered per cm of stigma. In a specific example, corn pollen was added to silks and incubated in a $KNO_3$ chamber for approximately 1 hour at about 25° C. and 96% humidity (Greenspan, *J Res NBS Phys Chem,* 81A:89-96, 1977), washed using a potassium phosphate buffer, fixed using a 3:1 ethanol:acetic acid solution overnight, and visualized using a stereoscope. Microscopic images were obtained and analyzed to determine the number of pollen grains adhered per cm silk (FIG. 17a-c). Importantly, the percentage of viable pollen in the sample as determined by mixing fresh, viable pollen with nonviable pollen directly correlates with the number of pollen grains adhered per cm silk (FIG. 17d).

Fertile pollen from virtually any plant may be evaluated using the methods described herein. Non-limiting examples of which include plants with recalcitrant pollen, dicot plants, monocot plants, cereal plants, Poaceae family plants, Alismataceae family plants, Amaranthaceae family plants, Cactaceae family plants, Chenopodiaceae family plants, Cucurbitaceae family plants, Anacardiaceae family plants, Portulacaceae family plants, Urticaceae family plants, Lauraceae family plants, Liliaceae family plants, Iridaceae family plants, Orchidaceae family plants, Acanthaceae family plants, Caryophyllaceae family plants, corn plants, rice plants, wheat plants, sorghum plants, and canola plants. In specific embodiments, the pollen may collected from a diploid, double haploid, or transformed plant. In one embodiment, the pollen may be collected from a $T_0$ transformed plant.

What is claimed is:
1. A continuous method for drying pollen comprising:
   a) providing a drying gas for continuously drying pollen;

b) providing a sensor to obtain at least one measurement in real-time during continuous drying that provides information regarding the moisture content of said pollen; and c) providing a processor in electronic communication with the sensor to calculate a slope of change in the moisture content of said pollen to determine when said pollen has reached a desired moisture content.

2. The method of claim 1, wherein the continuous drying of said pollen is stopped when the pollen has reached the desired moisture content.

3. The method of claim 1, wherein the at least one measurement is a wet basis moisture content measurement or a dry moisture content measurement of said pollen.

4. The method of claim 1, wherein the at least one measurement is obtained prior to said drying.

5. The method of claim 4, comprising determining the moisture content of the pollen prior to said drying.

6. The method of claim 1, wherein:

a) said desired moisture content is a wet basis moisture content between about 10% and about 35%; or b) said desired moisture content is a dry basis moisture content between about 17% and about 55%.

7. The method of claim 1, wherein the pollen is defined as;

a) pollen from a monocot plant;

b) pollen from a dicot plant; or c) recalcitrant pollen.

8. The method of claim 7, wherein the pollen is from a cereal plant.

9. The method of claim 8, wherein said cereal plant is a corn, rice, wheat, or sorghum plant.

10. The method of claim 1, further comprising storing the pollen after drying.

11. The method of claim 10, wherein:

a) said storing is performed at a temperature between about −196° C. and about −70° C.;

b) said storing is performed for up to about 10 years;

c) said storing is performed for at least about 1 hour, 1 day, 1 week, 1 month, 6 months, 1 year, 2 years, 5 years or 7 years;

d) at least about 1% of pollen grains remain capable of germination on a stigma following said storing; or e) wherein the pollen is defined as;

i) pollen from a monocot plant;

ii) pollen from a dicot plant; or iii) recalcitrant pollen.

12. The method of claim 11, wherein the pollen is from a cereal plant.

13. The method of claim 12, wherein said cereal plant is a corn, rice, wheat, or sorghum plant.

14. The method of claim 10, wherein the pollen is from a plant that is diploid, double haploid, or transformed.

15. The method of claim 10, wherein the pollen is stored short-term without the addition of any storage additive.

16. The method of claim 15, wherein the pollen is stored:

a) at a temperature between about 4.0° C. and about 10° C.; or b) at a relative humidity of between about 80% and about 100%.

17. The method of claim 1, further comprising pollinating a plant with said pollen.

18. The method of claim 17, wherein a) said pollinating produces at least about 1 seed per 1 mg of pollen used for said pollinating; or b) said pollinating produces a substantially equivalent number of seeds compared to the number of seeds produced from pollination under the same conditions but using pollen that was not subject to said drying.

19. The method of claim 17, wherein said pollinating occurs on two or more consecutive days.

20. The method of claim 1, wherein the sensor is measuring the moisture content of the drying gas.

21. The method of claim 1, wherein the sensor is in sufficient proximity to the chamber to obtain the moisture content measurement.

22. The method of claim 21, wherein the sensor is not in direct contact with the pollen within the chamber.

* * * * *